US012653472B2

(12) United States Patent
Lazarev et al.

(10) Patent No.: US 12,653,472 B2
(45) Date of Patent: Jun. 16, 2026

(54) TISSUE DIFFRACTOMETER FOR DETERMINING A DIAGNOSTIC INDICATOR

(71) Applicant: EosDx Inc., Menlo Park, CA (US)

(72) Inventors: Alexander P. Lazarev, Lake Forest, CA (US); Pavel Lazarev, Box Elder, SD (US)

(73) Assignee: EosDx Inc., Menlo Park, CA (US)

( * ) Notice: Subject to any disclaimer, the term of this patent is extended or adjusted under 35 U.S.C. 154(b) by 119 days.

(21) Appl. No.: 18/827,367

(22) Filed: Sep. 6, 2024

(65) Prior Publication Data

US 2026/0013812 A1     Jan. 15, 2026

(30) Foreign Application Priority Data

Jul. 12, 2024     (GB) ..................................... 2410187

(51) Int. Cl.
*A61B 6/00*          (2024.01)

(52) U.S. Cl.
CPC . *A61B 6/44* (2013.01); *A61B 6/48* (2013.01)

(58) Field of Classification Search
CPC .......... A61B 6/44; A61B 6/48; A61B 6/0407; A61B 6/50; A61B 6/5217
See application file for complete search history.

(56) References Cited

U.S. PATENT DOCUMENTS

| | | | |
|---|---|---|---|
| 5,479,927 A | 1/1996 | Shmulewitz | |
| 5,717,733 A | 2/1998 | Kurbatov et al. | |
| 5,849,595 A | 12/1998 | Alfano et al. | |
| 6,175,117 B1 | 1/2001 | Komardin et al. | |

(Continued)

FOREIGN PATENT DOCUMENTS

| | | |
|---|---|---|
| CN | 107106998 A | 8/2017 |
| CN | 112951416 A | 6/2021 |

(Continued)

OTHER PUBLICATIONS

Miah et al. ("On-cloud healthcare clinic: an e-health consultancy approach for remote communities in a developing country." Telematics and Informatics 34.1 (2017): 311-322 (Year: 2017).

(Continued)

*Primary Examiner* — Casey Bryant
(74) *Attorney, Agent, or Firm* — MLO, a professional corp.

(57)          ABSTRACT

The present disclosure provides systems and methods for determining one or more diagnostic indicators using X-ray diffraction (XRD). In some embodiments, the techniques described herein relate to a system including: a fixture configured to position a region of skin of a patient within a measurement region; an X-ray source coupled to the fixture and configured to emit an X-ray beam that overlaps with the measurement region; an X-ray receiver coupled to the fixture, the X-ray receiver including a coordinate-sensitive digital detector of X-rays; and one or more processors coupled to the X-ray receiver. The one or more processors can be configured to collect XRD data from the X-ray receiver, to process the XRD data, and to determine a diagnostic indicator for assessment of a physiological or pathological condition based on the processed XRD data.

13 Claims, 27 Drawing Sheets

(56)                 References Cited

U.S. PATENT DOCUMENTS

| | | | |
|---|---|---|---|
| 6,483,891 | B1 | 11/2002 | Lazarev et al. |
| 9,529,974 | B2 | 12/2016 | Li et al. |
| 11,522,703 | B1 | 12/2022 | Jain et al. |
| 2003/0014418 | A1 | 1/2003 | Adler et al. |
| 2003/0135096 | A1 | 7/2003 | Dodds |
| 2004/0258202 | A1 | 12/2004 | Wernick et al. |
| 2006/0015265 | A1 | 1/2006 | Raich |
| 2007/0032832 | A1 | 2/2007 | Feher |
| 2008/0147554 | A1 | 6/2008 | Stevens et al. |
| 2013/0208966 | A1 | 8/2013 | Zhao et al. |
| 2015/0269323 | A1 | 9/2015 | Ginsburg |
| 2015/0369759 | A1 | 12/2015 | Mazor et al. |
| 2016/0203263 | A1 | 7/2016 | Maier et al. |
| 2016/0235372 | A1 | 8/2016 | Schneider et al. |
| 2017/0362585 | A1 | 12/2017 | Wang et al. |
| 2018/0038845 | A1 | 2/2018 | Zimmermann et al. |
| 2018/0122499 | A1 | 5/2018 | Austin et al. |
| 2019/0046039 | A1 | 2/2019 | Ramesh et al. |
| 2019/0113451 | A1 | 4/2019 | Weissleder et al. |
| 2019/0271044 | A1 | 9/2019 | Stephan et al. |
| 2020/0098476 | A1 | 3/2020 | Loscutoff et al. |
| 2020/0160980 | A1 | 5/2020 | Lyman et al. |
| 2020/0242760 | A1 | 7/2020 | Holmes |
| 2022/0008027 | A1 | 1/2022 | Lazarev et al. |
| 2022/0013227 | A1 | 1/2022 | Lazarev et al. |
| 2022/0013233 | A1 | 1/2022 | Lazarev et al. |
| 2022/0399126 | A1 | 12/2022 | John et al. |
| 2022/0415505 | A1 | 12/2022 | Lazarev et al. |
| 2023/0113064 | A1 | 4/2023 | Yuk et al. |
| 2023/0240635 | A1 | 8/2023 | Lazarev et al. |
| 2023/0270396 | A1 | 8/2023 | Lazarev et al. |
| 2023/0341340 | A1* | 10/2023 | Lazarev ............... G01N 23/223 |
| 2024/0000412 | A1 | 1/2024 | Lazarev et al. |
| 2024/0016462 | A1 | 1/2024 | Lazarev et al. |
| 2024/0161893 | A1 | 5/2024 | Lazarev et al. |
| 2025/0149170 | A1 | 5/2025 | Lazarev et al. |

FOREIGN PATENT DOCUMENTS

| | | | |
|---|---|---|---|
| CN | 113012823 | A | 6/2021 |
| CN | 113533399 | A | 10/2021 |
| CN | 114599407 | A | 6/2022 |
| JP | H0933700 | A | 2/1997 |
| KR | 20180076702 | A | 7/2018 |
| WO | 2004071295 | A1 | 8/2004 |
| WO | 2005112752 | A1 | 12/2005 |
| WO | 2012048000 | A2 | 4/2012 |
| WO | 2013131156 | A1 | 9/2013 |
| WO | 2018081884 | A1 | 5/2018 |
| WO | 2021257451 | A1 | 12/2021 |
| WO | 2021257457 | A1 | 12/2021 |

OTHER PUBLICATIONS

Notice of Allowance and Fees dated Dec. 2, 2025 for U.S. Appl. No. 18/352,094.

Notice of Allowance and Fees dated Oct. 21, 2025 for U.S. Appl. No. 18/298,228.

Office Action dated Nov. 26, 2025 for U.S. Appl. No. 18/500,616.

Office Action dated Oct. 30, 2025 for U.S. Appl. No. 18/352,085.

Choi Mina et al: "Feasibility of imaging amyloid in the brain using small-angle x-ray scattering", Biomedical Physics & Engineering Express, vol. 7, No. 1,Nov. 27, 2020 (Nov. 27, 2020), p. 015008, XP093329220, GB ISSN: 2057-1976, DOI:10.1088/2057-1976/ab501c abstract section "2. Methods".

International Search Report and Written Opinion dated Nov. 7, 2025 for PCT Patent Application No. PCT/IB2025/056737.

Office Action dated Apr. 8, 2025 for U.S. Appl. No. 18/500,624.

Office Action dated Jun. 16, 2025 for U.S. Appl. No. 18/298,190.

Office Action dated Jun. 16, 2025 for U.S. Appl. No. 18/298,218.

Office Action dated Jun. 3, 2025 for U.S. Appl. No. 18/500,604.

Office Action dated Jul. 25, 2025 for U.S. Appl. No. 18/352,085.

Office Action dated Jul. 25, 2025 for U.S. Appl. No. 18/352,094.

Office Action dated Oct. 9, 2025 for U.S. Appl. No. 18/298,218.

Ahmadian et al., "Monitoring of drug resistance towards reducing the toxicity of pharmaceutical compounds: Past, present and future", Journal of Pharmaceutical and Biomedical Analysis, Mar. 19, 2020, 12 pgs.

Alfenaar, et al., "Therapeutic Drug Monitoring in Non Tuberculosis Mycobacteria Infections", Clinical Pharmacokinetics, Mar. 10, 2021, 15 pgs.

Arboleda et al, Assessing lesion malignancy by scanning small-angle X-ray scattering of breast tissue with microcalcifications, Phys Med Biol. Aug. 7, 2019;64(15):155010, pp. 1-9.

Buclin et al., "The Steps to Therapeutic Drug Monitoring: A Structured Approach Illustrated With Imatinib", Frontiers in Pharmacology, vol. 11, Article 177, Mar. 3, 2020, 10 pgs.

Chapman et al., Diffraction enhanced x-ray imaging, Phys. Med. Biol. 42, Nov. 1997, pp. 2015-2025.

Conceicao et al, Analysis of breast cancer by small angle X-ray scattering (SAXS), Analyst, Apr. 2009 134 (6):1077-82.

European Search Report dated May 24, 2024 for European Patent Office Patent Application No. 21826535.3.

Fagundes et al., "Structural characterization of canine mammary tissue by x-ray diffraction", Radiation Physics and Chemistry, vol. 155, pp. 22-25. (Year: 2019).

Frolov et al., "Risk stratification personalised model for prediction of life-threatening ventricular tachyarrhythmias in patients with chronic heart failure," Kardiologia Polska Mar. 2017; 75, 7: 682-688; DOI: 10.5603/KP.a2017.0060.

Ghammraoui et al., "Maximum-likelihood estimation of scatter components algorithm for x-ray coherent scatter computed tomography of the breast", Physics in Medicine & Biology, vol. 61, pp. 3164-3179. (Year: 2016).

Ghiculescu, "Therapeutic drug monitoring: which drugs, why, when and how to do it", Australian Prescriber, vol. 31, No. 2, Apr. 2008, pp. 42-44.

Graewet et al., "Impact and progress in small and wide angle X-ray scattering (SAXS and WAXS)", Current Opinion in Structural Biology, vol. 23, pp. 748-754. (Year: 2013).

Iacuzzi et al., "Dried Blood Spot Technique Applied in Therapeutic Drug Monitoring of Anticancer Drugs: a Review on Conversion Methods to Correlate Plasma and Dried Blood Spot Concentrations", Pharm Res, Springer, Apr. 12, 2021, 20 pgs.

James, "A Review of Low Angle Fibre Diffraction in the Diagnosis of Disease", British Journal of Medicine & Medical Research, 3(2): 383-397, Feb. 19, 2013.

James, "Fiber diffraction of skin and nails provides an accurate diagnosis of malignancies", Int. J. Cancer: 125, 133-138, 13 pages, Jul. 2009.

James, "Fiber diffraction of skin and nails provides an accurate diagnosis of malignancies", Int. J. Cancer: 125, Feb. 2009, pp. 133-138.

Kuwayama et al., "Time-course measurements of drug concentrations in hair and toenails after single administrations of pharmaceutical products", Drug Testing and Analysis, Jun. 24, 2016, 7 pgs, John Wiley & Sons, Ltd.

Lazarev et al., "Human Tissue X-ray Diffraction: Breast, Brain, and Prostate", Proceedings of the 22nd Annual International Conference of the IEEE Engineering in Medicine and Biology Society, Cat. No. 00CH37143, vol. 4, Jul. 2000, pp. 3230-3233.

Lupien et al., "Effects of stress throughout the lifespan on the brain, behaviour and cognition", Focus on Stress, Jun. 2009, 12 pgs, Macmillan Publishers Limited.

Moss et al., Correlation of X-ray diffraction signatures of breast tissue and their histopathological classification, Scientific Reports, Oct. 2017, pp. 1-9.

Notice of Allowance and Fees dated Feb. 6, 2023 for U.S. Appl. No. 17/593,846.

Notice of Allowance and Fees dated Jul. 19, 2023 for U.S. Appl. No. 17/448,888.

Notice of Allowance and Fees dated May 20, 2024 for U.S. Appl. No. 17/448,886.

Office Action dated Feb. 26, 2024 for U.S. Appl. No. 17/448,886.

Office Action dated Mar. 22, 2023 for U.S. Appl. No. 17/448,888.

(56)                References Cited

OTHER PUBLICATIONS

Oliver et al., Diffraction enhanced imaging utilizing a laser produced x-ray source, Rev. Sci. Instrum. 93, 093502, Sep. 2022, 7 pages.

Ong et al., "Optical biosensors—Illuminating the path to personalized drug dosing", Biosensors and Bioelectronics, May 13, 2021, 21 pgs.

Ortin et al., "Automated real-time method for ventricular heartbeat classification," Computer Methods and Programs in Biomedicine 169 (2019) 1-8, Nov. 2018, 8 pages.

Ortiz et al, "Biomarkers of disease in human nails: a comprehensive review", Critical Reviews in Clinical Laboratory Sciences, Oct. 7, 2021, 18 pgs, Taylor & Francis Group.

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, Written Opinion of the InternationalSearching Authority in connection with related International Application No. PCT/US2021/037238, dated Oct. 5, 2021, 5 pgs.

Rodriguez, Kari, Authorized Officer, Commissioner for Patents, "International Search Report" in connection with related International Application No. PCT/US2021/037224, dated Sep. 29, 2021, 3 pgs.

Rodriguez, Kari, Authorized Officer, Commissioner for Patents, Written Opinion of the International Searching Authority in connection with related International Application No. PCT/US2021/037224, dated Sep. 29, 2021, 6 pgs.

Round et al., A preliminary study of breast cancer diagnosis using laboratory based small angle x-ray scattering, Phys Med Biol. Sep. 2005, 50(17):4159-68.

Sidhu et al., Mapping structural changes in breast tissue disease using x-ray scattering, Medical Physics 36, May 2009, pp. 3211-3217.

Todd et al., "Survival in dementia and predictors of mortality: a review", International Journal of Geriatric Psychiatry, Mar. 2013, 16pgs, John Wiley & Sons, Ltd.

Visser, "Techniques for Monitoring Drug Efficacy", Vet Clin North Am Exot Anim Pract., 21(2), May 2018, 287-295, 2018, 7pgs.

Wallenburg et al., "Personalised antimicrobial dosing: standing on the shoulders of giants", International Journal of Antimicrobial Agents, Sep. 2020, 18 pgs.

Wang et al., "A High Precision Real-time Premature Ventricular Contraction Assessment Method based on the Complex Feature Set," Journal of Medical Systems (2020) 44:3, published Nov. 2019, 16 pages.

Wiencek, et al., "Rapid Assessment of Drugs of Abuse", Advances in Clinical Chemistry, Dec. 2016, 33 pgs, Elsevier Inc., Nashville, TN.

Wu et al., "ECG signal classification with binarized convolutional neural network," Computers in Biology and Medicine 121, 103800, May 2020, 9 pages.

Yoneyama et al., Fast diffraction-enhanced imaging using continuous sample rotation and analyzer crystal scanning, J Synchrotron Radiat, Mar. 2020, pp. 468-471.

Zheng et. al., "Recent advances in drug release monitoring", Nanophotonics, 8(3), Feb. 2009, pp. 391-413.

European Search Report dated Dec. 4, 2024 for United Kingdom Patent Application No. 2410187.5.

European Search Report dated Dec. 5, 2024 for United Kingdom Patent Application No. 2410185.9.

International Search Report and Written Opinion dated Jan. 17, 2025 for PCT Patent Application No. PCT/IB2024/059571.

International Search Report and Written Opinion dated Jan. 23, 2025 for PCT Patent Application No. PCT/IB2024/060284.

International Search Report and Written Opinion dated Jan. 23, 2025 for PCT Patent Application No. PCT/IB2024/060286.

International Search Report and Written Opinion dated Jan. 31, 2025 for PCT Patent Application No. PCT/IB2024/060287.

Notice of Allowance and Fees dated Dec. 22, 2025 for U.S. Appl. No. 18/298,218.

Notice of Allowance and Fees dated Jan. 30, 2026 for U.S. Appl. No. 18/352,085.

Office Action dated Dec. 8, 2025 for U.S. Appl. No. 18/500,604.

* cited by examiner

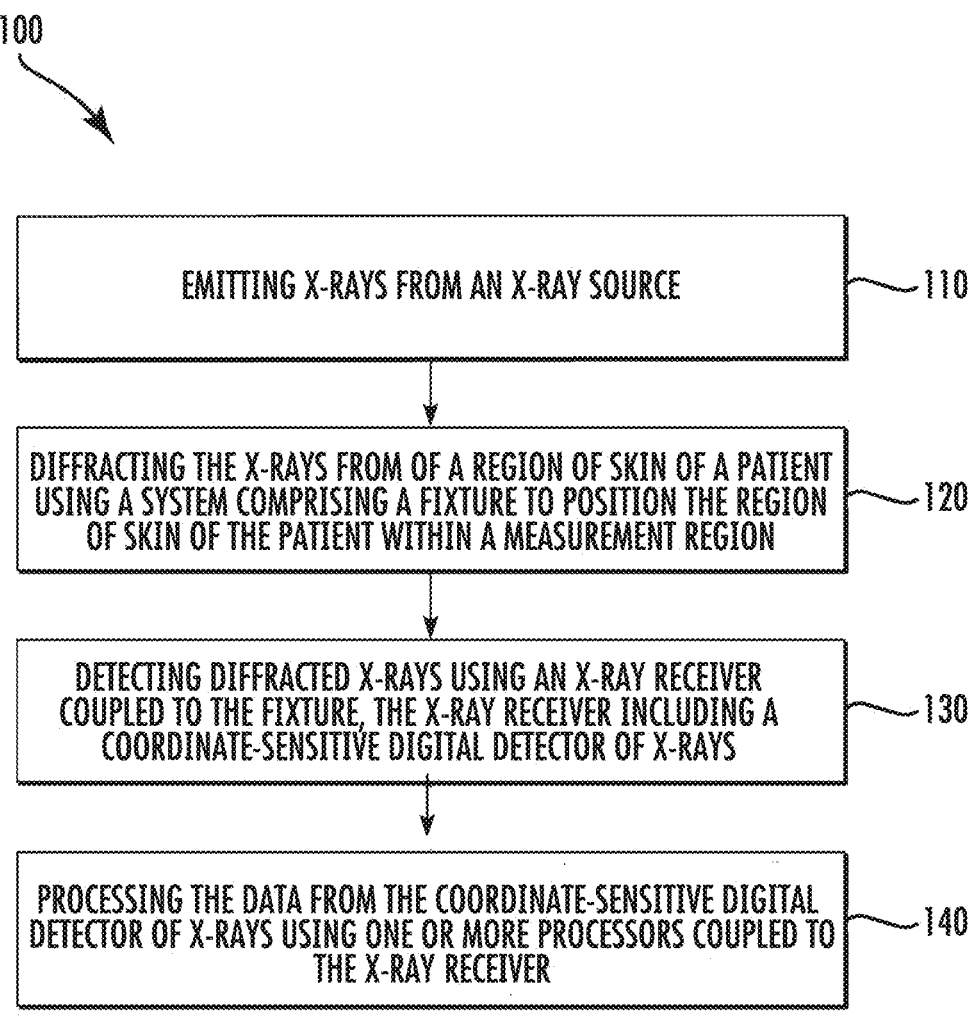

100

EMITTING X-RAYS FROM AN X-RAY SOURCE — 110

DIFFRACTING THE X-RAYS FROM OF A REGION OF SKIN OF A PATIENT USING A SYSTEM COMPRISING A FIXTURE TO POSITION THE REGION OF SKIN OF THE PATIENT WITHIN A MEASUREMENT REGION — 120

DETECTING DIFFRACTED X-RAYS USING AN X-RAY RECEIVER COUPLED TO THE FIXTURE, THE X-RAY RECEIVER INCLUDING A COORDINATE-SENSITIVE DIGITAL DETECTOR OF X-RAYS — 130

PROCESSING THE DATA FROM THE COORDINATE-SENSITIVE DIGITAL DETECTOR OF X-RAYS USING ONE OR MORE PROCESSORS COUPLED TO THE X-RAY RECEIVER — 140

FIG. 1

200

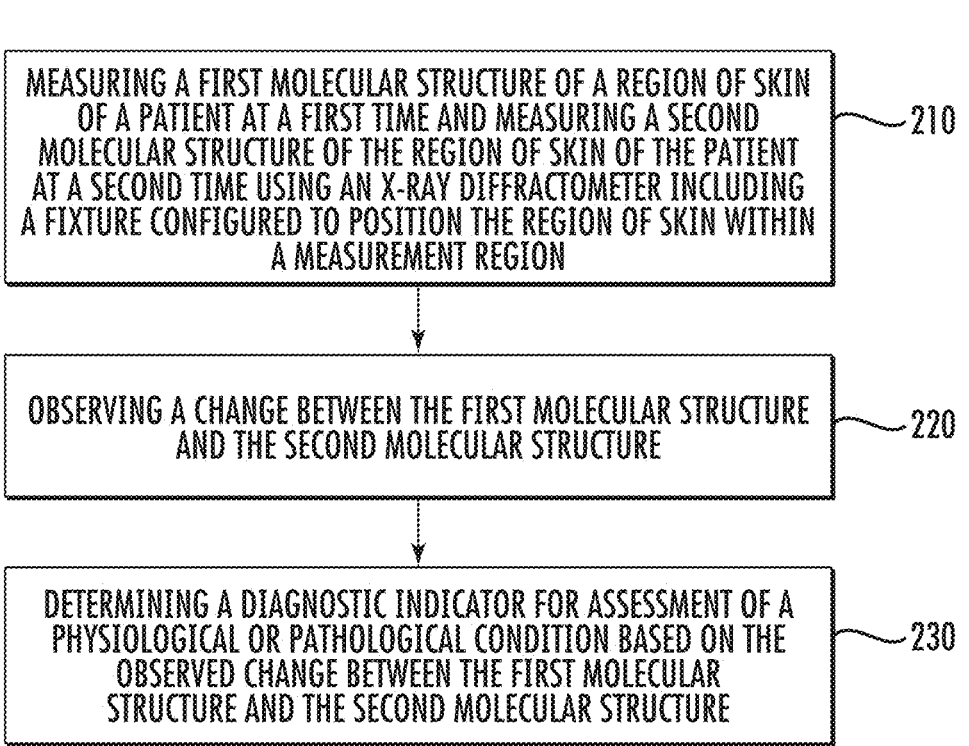

MEASURING A FIRST MOLECULAR STRUCTURE OF A REGION OF SKIN OF A PATIENT AT A FIRST TIME AND MEASURING A SECOND MOLECULAR STRUCTURE OF THE REGION OF SKIN OF THE PATIENT AT A SECOND TIME USING AN X-RAY DIFFRACTOMETER INCLUDING A FIXTURE CONFIGURED TO POSITION THE REGION OF SKIN WITHIN A MEASUREMENT REGION — 210

OBSERVING A CHANGE BETWEEN THE FIRST MOLECULAR STRUCTURE AND THE SECOND MOLECULAR STRUCTURE — 220

DETERMINING A DIAGNOSTIC INDICATOR FOR ASSESSMENT OF A PHYSIOLOGICAL OR PATHOLOGICAL CONDITION BASED ON THE OBSERVED CHANGE BETWEEN THE FIRST MOLECULAR STRUCTURE AND THE SECOND MOLECULAR STRUCTURE — 230

SKIN WEB

524a

540

527a

521

522a

560

505

510

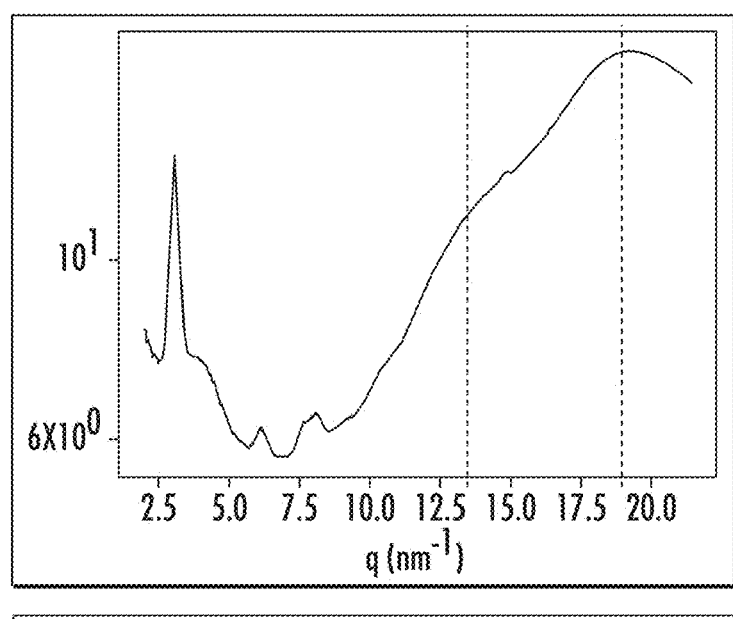
*FIG.* 14E
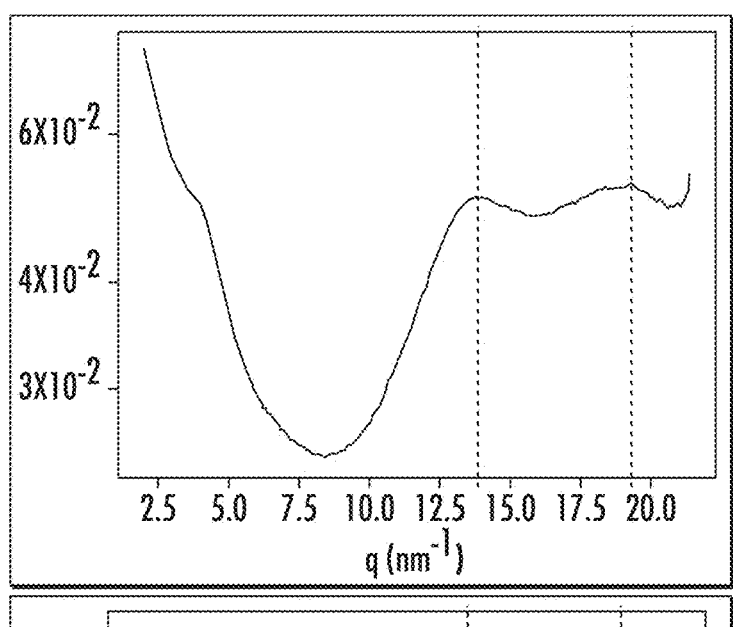
*FIG.* 14F
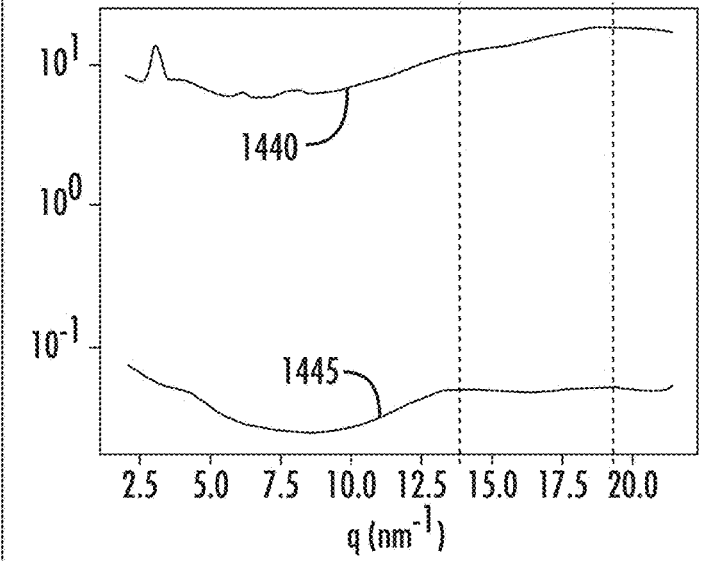
*FIG.* 14G

TISSUE DIFFRACTOMETER FOR DETERMINING A DIAGNOSTIC INDICATOR

RELATED APPLICATIONS

This application claims priority to United Kingdom Patent Application Serial No. GB 2410187.5, filed Jul. 12, 2024, and entitled "Tissue Diffractometer for Determining a Diagnostic Indicator", the content of which is hereby incorporated by reference in its entirety.

BACKGROUND

Early diagnosis of severe pathological conditions, such as breast cancer, acute myocardial infarction, pericarditis and bradycardia of the heart, and ischemic and neurological strokes, is directly related to the successful treatment of a patient. There have been some efforts at the early detection and diagnosis of some types of diseases in humans and animals. Some have been "direct" methods to detect disease in human prostate, breast and brain tissue, and some have been "indirect" detection and diagnostic methods utilizing hair or nail samples to detect certain diseases.

Fiber diffraction patterns of skin or fingernails, using X-ray sources, have been used as a biometric diagnostic method for detecting neoplastic disorders such as melanoma, breast cancer, colon cancer and prostate cancer. It may be possible to conduct such tests at local radiology facilities (e.g., as a confirmatory test for other diagnostic procedures), or as a mass screening test using small angle X-ray beam-lines at synchrotron radiation facilities.

In another example, small-angle x-ray diffraction was used to study the structure of potential cancer sites in human prostate, breast and brain tissue. Diffraction patterns at small angles corresponded to large diffracting structures in the tissue material, and each tissue had a different and distinct diffraction pattern. Further, for a particular tissue, it was found that patterns from normal and pathological samples were different from each other.

SUMMARY

In some embodiments, the techniques described herein relate to a system including: a fixture configured to position a region of skin of a patient within a measurement region; an X-ray source coupled to the fixture and configured to emit an X-ray beam that overlaps with the measurement region; an X-ray receiver coupled to the fixture, the X-ray receiver including a coordinate-sensitive digital detector of X-rays; and one or more processors coupled to the X-ray receiver; wherein the one or more processors are configured to control the X-ray source and the X-ray receiver, to collect X-ray diffraction data from the X-ray receiver, to process the X-ray diffraction data, and to determine a diagnostic indicator for assessment of a physiological or pathological condition based on the processed X-ray diffraction data.

BRIEF DESCRIPTION OF THE DRAWINGS

FIG. 1 is a flowchart of an example of a method for determining a diagnostic indicator for assessment of one or more physiological or pathological conditions, in accordance with some embodiments.

FIG. 2A is a flowchart of an example of a method for determining a diagnostic indicator for assessment of one or more physiological or pathological conditions, in accordance with some embodiments.

FIGS. 14A-14K compare the synchrotron data of this Example with XRD data obtained using an X-ray diffractometer like that of FIG. 4 described in Example 1.

DETAILED DESCRIPTION

Figure 2B:
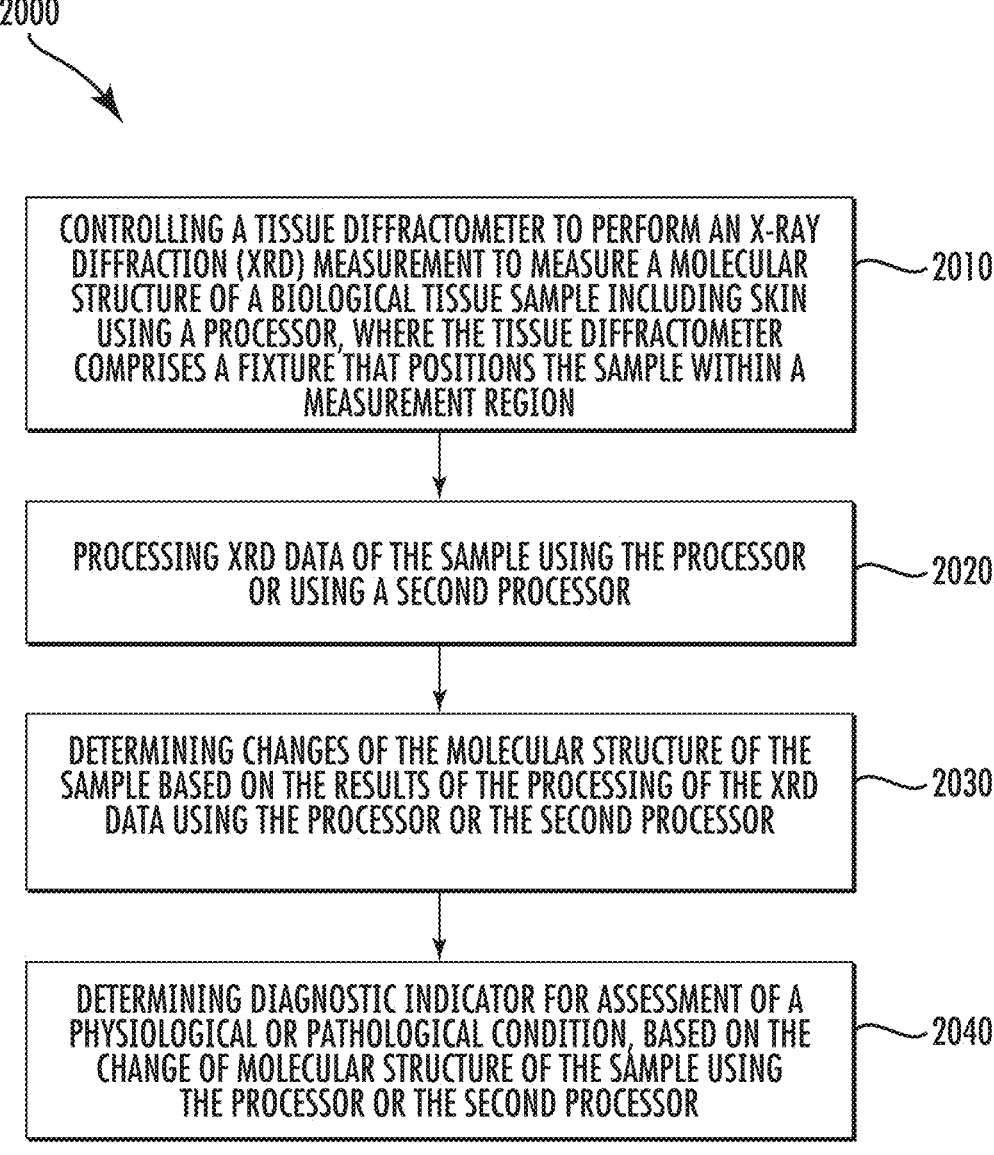
FIG. 2B is a flowchart of an example method for determining a diagnostic indicator for assessment of one or more physiological or pathological conditions, in accordance with some embodiments.

The present disclosure provides systems and methods for determining one or more diagnostic indicators for assessment of one or more physiological or pathological conditions using X-ray diffraction (XRD). XRD from a biological tissue sample of a patient can be measured by a tissue diffractometer, and the resulting XRD data can be analyzed by a processor to produce a diagnostic indicator for assessment of one or more physiological or pathological conditions.

The biological tissue sample can include a region of skin, in some cases, and the tissue diffractometer can include a fixture to position the region of skin within a measurement region. In some cases, the biological tissue sample can be measured in vivo, and the fixture can position a portion of the patient's body (e.g., their hand) such that the region of skin is positioned within a measurement region. In other cases, the biological tissue sample can be measured in vitro, and the fixture can position a sample (e.g., a sample resected from the patient) such that the region of skin is positioned within a measurement region.

The "biological tissue" or "biological tissue sample" measured by X-ray diffraction using a tissue generally refers to tissue (or tissue samples) of a patient. For example, biological tissue can include materials of living organs that contain structural molecular components and functional components like cells, muscles, and skin, as well as detachable structures like nails and hairs. In some cases, biological tissue can contain biological molecular structures such as lipids, collagens, keratins and glycoproteins that diffract X-ray light.

The XRD measurements can include small-angle X-ray scattering (SAXS) measurements and/or wide-angle X-ray scattering (WAXS) measurements. For example, the tissue diffractometers can have fixed or adjustable distances between the sample and a detector to detect different angular ranges of diffracted X-rays. In some cases, the XRD measurements can be grazing incidence XRD measurements, in either SAXS or WAXS configurations. Grazing incidence XRD provides improved sensitivity to materials close to the surface, which can be advantageous when measuring XRD from skin, since it is at the surface of the tissue sample.

In some cases, the diagnostic indicators for assessment of one or more physiological or pathological conditions are determined by analyzing XRD data over time to observe or determine a change in the XRD data. For example, XRD data can be taken from a region of skin of a patient over time (e.g., over 2 days, 1 week, 10 days, 2 weeks, 1 month, 1 year, or other time duration). The XRD data can be analyzed to determine if there is a change in the XRD data between measurements, and an observed change can then be used to determine the diagnostic indicators for assessment of one or more physiological or pathological conditions.

In some cases, the XRD data from a single instance of time can be used to determine the diagnostic indicators for assessment of one or more physiological or pathological conditions. For example, the presence or absence of a peak at a particular q value could indicate the presence or absence of one or more physiological or pathological conditions. In another example, a ratio of intensities of a first peak at a first q value and a second peak at a second q value could indicate the presence or absence of one or more physiological or pathological conditions.

In some embodiments, the diffractometer of the systems and methods described herein includes a radiation source (or an X-ray source), a beam forming apparatus, an adjustable diaphragm, and a receiver of the X-rays comprising a filter and a two-dimensional detector. In some cases, the beam forming apparatus can include a Kratki or Montel mirror collimator. In some cases, the filter of the diffractometer is positioned to screen the two-dimensional detector from a transmitted portion of the beam, and/or the filter at least partially reduces an intensity of the transmitted portion of the beam. In some cases, the two-dimensional detector of the diffractometer includes a plurality of detector elements each of which provide a signal upon receiving X-rays (e.g., penetrating and/or scattered X-ray photons or radiation). In some cases, the position of the two-dimensional detector relative to the breast positioning area is such that each detector element is associated with a particular range of scattering angles. In some cases, the two-dimensional detector comprises a plurality of detector elements each of which provide a signal upon receiving X-ray radiation, and a position of the two-dimensional detector relative to the measurement area is such that some detector elements are associated with ranges of scattering angles of X-rays scattered by the biological tissue sample. In some embodiments, the X-ray systems described herein further comprise a position adjusting mechanism of the two-dimensional detector configured to move the detector relative to the measurement area.

In some embodiments, the digital flat-panel detector is a plate that comprises a two-dimensional sensitive matrix of X-ray-sensitive elements. Digital radiography systems can beneficially eliminate consumables and equipment for film. When using digital radiography systems, radiologists do not need to work with plates, film, developer, fixer and water. They do not need scanners, developing machines, drying equipment, digitizers and a darkened room with a temperature of at least 20° C. Digital radiography systems save money on consumables and space in the room. There are two main types of conversion of X-rays into an electrical signal: direct and indirect. In the first case, the X-ray radiation is immediately converted into a signal. In the second case, the radiation is first converted to light, and the light is converted to a signal. Detectors for industrial radiography typically use the second type of conversion. The scintillator is responsible for converting X-rays into light. As a scintillator, gadolinium oxysulfide or cesium iodide is usually used. A light-sensitive thin film transistor (TFT) or complementary metal-oxide semiconductor (CMOS) matrix converts light into electrons that charge or discharge a capacitor in each element of the matrices. When reading, the capacitors are discharged or charged, and an electric current is generated. The charging and discharging current of the capacitors is measured using an analog-to-digital converter (ADC). The resulting values are converted to the gray level for each of the pixels, and an image is formed from the pixels.

X-ray diffraction systems and methods for characterizing biological tissue samples are further described in U.S. patent application Ser. Nos. 17/593,846, 17/448,888, 18/056,219, and 18/500,616, which are hereby incorporated by reference in their entireties.

In some instances, the systems and methods described herein to determine a diagnostic indicator can include the use of one or more statistical algorithms. For example, points and features can be extracted from a global set of XRD data (e.g., using analytical methods, numerical methods, machine learning methods, etc.), and statistical algorithms can be used to categorize the data into the data clusters using the calculated metrics. The set of global XRD data is from a set of global patients, which can be from any location in the world, or from a specific geographical region or nation. The global XRD data can be stored in a global database. Statistical algorithms can also be used when comparing local XRD measurement data with the data clusters to determine a diagnostic indicator for a local patient. For example, the metrics of local XRD measurement data can be compared with the data clusters of the global XRD data to determine which data cluster the local measurement data is most closely associated. The diagnostic indicator for the local patient can then be determined to be the one that is associated with the closest data cluster. In some cases, a cluster center of each data cluster can be determined using statistical analyses, and the metrics of the local measurement data of a local patient (and in some cases the patient data) can be translated into a local data point which can be compared with the cluster centers. For example, the data cluster associated with local XRD measurement data can be the one that has the shortest distance between the local data point and the cluster center of that data cluster.

In some instances, a data analytics algorithm used by the systems and methods described herein to determine a diagnostic indicator can include the use of one or more machine learning algorithms. The one or more machine learning algorithms may be configured to operate upon local XRD measurement data, local patient data, global XRD data from a global database, patient data from a global database, or any combination thereof. The machine learning algorithm can include one or more supervised learning algorithms, one or more unsupervised learning algorithms, one or more semi-supervised learning algorithms, one or more reinforcement learning algorithms, one or more deep learning algorithms, or any combination thereof. The machine learning algorithm may be a deep learning algorithm. The deep learning algorithm can include one or more convolutional neural networks, one or more recurrent neural networks, and/or one or more recurrent convolutional neural networks.

In some embodiments of the systems and methods described herein, statistical analysis algorithms and/or machine learning algorithms can be implemented on a local computer (i.e., one that is local to an LAC, the GDC or the AC), or a remote server (e.g., one that is in the cloud, or in a distributed network of computers). For example, a machine learning algorithm can be configured to preprocess raw local XRD measurement data, and/or patient data to remove noise or other artifacts. A different machine learning algorithm can be trained to identify features within the local XRD measurement data, and/or patient data. Such a machine learning algorithm can cluster data points for use as an identification algorithm. Other machine learning algorithms can be configured to provide a diagnostic indicator for assessment of one or more physiological or pathological conditions.

The machine learning algorithms used by the systems and methods described herein may include a supervised, semi-supervised, or unsupervised machine learning algorithm. A supervised machine learning algorithm, for example, is an algorithm that is trained using labeled XRD training data sets, e.g., XRD data sets that comprise XRD training data with known outputs (e.g., if the corresponding patient has a particular physiological or pathological condition). The training inputs can be provided to an untrained or partially trained version of the machine learning algorithm to generate a predicted output. The predicted output can be compared to the known output in an iterative process, and if there is a difference, the parameters of the machine learning algorithm can be updated. A semi-supervised machine learning algorithm is trained using a large set of unlabeled XRD training data, e.g., unlabeled training inputs, and a small number of labeled XRD training inputs. An unsupervised machine learning algorithm, e.g., a clustering algorithm, may find previously unknown patterns in XRD data sets comprising XRD data with no pre-existing labels.

For example, a machine learning algorithm that can be used to perform some of the functions described above (e.g., processing of global XRD data, local XRD measurement data, patient data, and/or generating diagnostic indicators) is a neural network. Neural networks employ multiple layers of operations to predict one or more outputs, for example, a likelihood that a subject has a disease, from one or more inputs, for example, XRD measurement data, patient data, processed XRD data derived from XRD measurement data, and/or patient data, or any combination thereof. Neural networks can include one or more hidden layers situated between an input layer and an output layer. The output of each layer can be used as input to another layer (e.g., the next hidden layer or the output layer). Each layer of a neural network can specify one or more transformation operations to be performed on the data input to the layer. Such transformation operations may be referred to as "neurons." The output of a particular neuron may be, for example, a weighted sum of the inputs to the neuron, that is optionally adjusted with a bias and/or multiplied by an activation function (e.g., a rectified linear unit (ReLU) or a sigmoid function).

Training a neural network that can be used to perform some of the functions described above (e.g., processing of global XRD data, local XRD measurement data, patient data, and/or generating diagnostic indicators) can involve providing inputs to the untrained neural network to generate predicted outputs, comparing the predicted outputs to expected outputs, and updating weights and biases of the algorithm in an iterative manner to account for the difference between the predicted outputs and the expected outputs. For example, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, such as obtaining a small magnitude of calculated cost.

Convolutional neural networks (CNNs) and recurrent neural networks can be used to process, analyze, classify, or make predictions from global XRD data, local XRD measurement data, patient data, or any combination thereof. CNNs are neural networks in which neurons in some layers, called convolutional layers, receive data from only small portions of a data set. These small portions may be referred to as the receptive fields of the neurons. Each neuron in such a convolutional layer may have the same weights. In this way, the convolutional layer can detect features, e.g., diagnose changes in myocardium, in any portion of the input measurement data.

RNNs, meanwhile, are neural networks with cyclical connections that can encode dependencies in time-series data, and can be used to perform some of the functions described herein, for example, those related to local XRD measurement data collected over time, and longitudinal studies of one or more patients. An RNN may include an input layer that is configured to receive a sequence of time-series inputs, e.g., local XRD measurement data, patient data, or any combination thereof collected over a period of time. An RNN may also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. In some cases, such an RNN can be used to determine time-series features or evolutions of features within local XRD measurement data and/or patient data.

An example of an RNN that can be used to perform some of the functions described herein is a long short-term memory network (LSTM), which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate may be, for example, the logistic function.

Other examples of machine learning algorithms that can be used to perform some of the functions described herein (e.g., to process and categorize global XRD data, local XRD measurement data, patient data, or any combination thereof) are regression algorithms, decision trees, support vector machines, Bayesian networks, clustering algorithms, reinforcement learning algorithms, and the like.

For example, a clustering algorithm can be used, which can be a hierarchical clustering algorithm in some cases. A hierarchical clustering algorithm can be a clustering algorithm that clusters patients based on their proximity to other patients. For example, a hierarchical clustering algorithm can cluster global XRD data, local XRD measurement data, patient data, or any combination thereof. The clustering algorithm can alternatively be a centroid-based clustering algorithm, for example, a k-means clustering algorithm. A k-means clustering algorithm can partition a set of (n) observations into a set of (k) data clusters, where each observation belongs to the data cluster with the nearest mean. The mean can serve as a prototype for the data cluster. In the context of global data, local measurement data, patient data, or any combination thereof, a k-means clustering algorithm can generate distinct groups of data that are correlated with each other. Thereafter, each group of data can be associated with a particular data cluster, based on knowledge about that subsystem (e.g., knowledge about previous diagnoses and data). As described herein, each data cluster can be associated with a diagnostic indicator, which can be, for example, a probability or diagnosis of a condition (e.g., of a disease described herein). For example, each data cluster can correspond to a diagnostic indicator including a probability score for the likelihood of one or more physiological or pathological conditions (e.g., cancer, or a cardiac condition, or both). The clustering algorithm can alternatively be a distribution-based clustering algorithm, for example, a Gaussian mixture model or expectation maximization algorithm. Examples of other clustering algorithms are cosine similarity algorithms, topological data analysis algorithms, and hierarchical density-based clustering of applications with noise (HDB-SCAN).

The machine learning algorithms that can be used to perform some of the functions described herein (e.g., to process and categorize global XRD data, local XRD measurement data, patient data, or any combination thereof) can be trained using a training dataset comprising global XRD data, local XRD measurement data, patient data, or any combination thereof. The training dataset may be stored in a computer database of the system (e.g., the global database) for a specific pathology and/or physiological norm group. The training dataset may be obtained using local XRD measurement data provided for the analysis, or the training dataset can include global XRD data, local XRD measurement data, and/or patient data from any source (e.g., a government-operated database). The training dataset can include information regarding a confirmation of a diagnosis for a given set of XRD data. The computer database of the systems and methods described herein for a specific pathology and/or physiological norm group may be a remote computer database (e.g., a cloud-based database) or a local database (e.g., a computer system local to tissue diffractometer).

The training dataset may be updated as new global XRD data, local XRD measurement data, patient data, or any combination thereof is uploaded to a global database storing the global XRD data. The updating may be an inclusion of the new data, a removal of the old data, or a combination thereof. For example, new patient data can be added to the training dataset as it is taken (e.g., in real-time, or substantially real-time) or after it is taken to improve the quality of the training dataset. In another example, poor quality data may be removed from the training dataset when higher quality new data is added. The statistical analysis algorithm and/or machine learning algorithm (e.g., the data analytics algorithm) used by the systems and methods described herein may be updated when the computer database or training dataset residing thereon is updated. For example, a machine learning algorithm can be retrained using the new training dataset to improve the efficacy of the machine learning algorithm in generating a computer-aided diagnostic indicator. The statistical analysis and/or machine learning algorithm may be continuously, periodically, or randomly updated and refined as the training dataset is updated. In this example, the revised statistical analysis and/or machine learning algorithm may be more accurate, specific, and/or sensitive in providing a probability or diagnosis than a previous version derived from a previous training dataset.

The systems and methods described herein can be used to determine a diagnostic indicator for assessment of one or more physiological or pathological conditions of a local patient. The diagnostic indicators can include an indicator of a likelihood that the local patient has a disease, such as cancer, heart disease, or other disease described herein. For example, a diagnostic indicator can include a banded risk assessment for the local patient (e.g., high risk, medium risk, low risk). The computer-aided diagnostic indicator may be displayed on a user interface of a computer or device in communication with the processor that is used to determine the diagnostic indicator. The diagnostic indicator may be a report in some cases. The report may be a printed report, and it can include additional information. For example, the report can include a likelihood of the patient having one or more physiological or pathological conditions (e.g., chronic lung disease, or prostate cancer), as well as the indicators that contributed to the generation of the report and a suggestion of possible next steps for the patient to take. The diagnostic indicator may be a percentage (e.g., a percentage likelihood that the patient has the disease), a risk band (e.g., high risk, medium risk, low risk), comparison of factors (e.g., a list of factors indicating a presence and a list of factors indicating an absence), or the like, or any combination thereof. For example, a diagnostic indicator can contain an indicator of the likelihood that the individual patient has a disease (e.g., chronic lung disease), which may be an indicator of the likelihood that the individual patient has another condition or disease (e.g., thromboembolism).

In some cases, a diagnostic indicator described herein may contain a diagnosis that the local patient has a disease, such as those described herein. A computer-aided diagnostic indicator for an individual patient may contain a diagnosis that an individual patient has a disease. A diagnostic indicator can be generated, at least partially, using a statistical analysis algorithm and/or a machine learning algorithm. A diagnostic indicator can be generated, at least in part, using the input data of a healthcare provider. For example, a health care provider may be presented with a list of indicators and risk ranges, and the health care provider may make a final decision regarding the patient's diagnosis. In such cases, the global database used to establish the XRD data clusters can also be provided by the health care provider. In some cases, a diagnostic indicator of the diagnostic systems and methods described herein may have accuracy, selectivity and/or specificity of at least about 10%, 20%, 30%, 40%, 50%, 60%, 70%, 80%, 90%, 95%, 98%, 99%, 99.9%, or more. In some cases, the diagnostic indicator may have accuracy, selectivity and/or specificity of no more than 99.9%, 99%, 98%, 95%, 90%, 80%, 70%, 60%, 50%, 40%, 30%, 20%, 10%, or less. Any of the lower and upper values described in this paragraph can be combined to form the range of the accuracy, selectivity and/or specificity of the diagnostic indicator, for example, in some cases, a diagnostic indicator may have accuracy, selectivity and/or specificity that ranges from about 80% to about 99%. A diagnostic indicator may have accuracy, selectivity and/or specificity that has any value in this range, for example, about 98.6%.

FIG. 1 is a flowchart of an example of a method 100 for processing X-ray diffraction data, in accordance with some embodiments. At block 110, X-rays are emitted from an X-ray source. At block 120, the X-rays are diffracted from of a region of skin of a patient using a system comprising a fixture configured to position the region of skin of the patient within a measurement region. At block 130, diffracted X-rays are detected using an X-ray receiver coupled to the fixture. The X-ray receiver can include a coordinate-sensitive digital detector of X-rays. At block 140, the data from the coordinate-sensitive digital detector of X-rays is processed using one or more processors coupled to the X-ray receiver. The data from the coordinate-sensitive digital detector of X-rays can be processed to determine a diagnostic indicator for assessment of one or more physiological or pathological conditions. For example, the diagnostic indicator can include a probability score for the likelihood of one or more physiological or pathological conditions (e.g., cancer, or a cardiac condition, or both).

FIG. 2A is a flowchart of an example of a method 200 for determining a diagnostic indicator for assessment of one or more physiological or pathological conditions, in accordance with some embodiments. At block 210 a first molecular structure of a region of skin of a patient is measured at a first time and a second molecular structure of the region of skin of the patient is measured at a second time using an X-ray diffractometer including a fixture configured to position the region of skin within a measurement region. At block 220, a change is observed between the first molecular structure and the second molecular structure. At block 230, the diagnostic indicator for assessment of one or more physiological or pathological conditions is determined based on the observed change between the first molecular structure and the second molecular structure. In some cases, the diagnostic indicator can include a probability score for the likelihood of one or more physiological or pathological conditions (e.g., cancer, or a cardiac condition, or both).

FIG. 2B is a flowchart of an example method 2000 for determining a diagnostic indicator for assessment of one or more physiological or pathological conditions, in accordance with some embodiments. At block 2010 a tissue diffractometer is controlled using a processor to perform an X-ray diffraction (XRD) measurement to measure a molecular structure of a biological tissue sample including skin, where the tissue diffractometer comprises a fixture that positions the sample within a measurement region. At block 2020, XRD data of the sample is processed using the processor or using a second processor. For example, the XRD data can be averaged, noise can be subtracted, and/or peaks can be fit with Gaussian functions in order to determine peak positions and/or the breadth (e.g., FWHM) of the peaks. At block 2030, a change of the molecular structure of the sample is determined based on the results of the processing of the XRD data using the processor or the second processor. At block 2040, a diagnostic indicator for assessment of one or more physiological or pathological conditions is determined, based on the change of the molecular structure of the sample using the processor or the second processor. In some cases, the diagnostic indicator can include a probability score for the likelihood of one or more physiological or pathological conditions (e.g., cancer, or a cardiac condition, or both). Physiological or pathological conditions such as cancer (e.g., melanoma, breast, colon, and prostate cancers) and Alzheimer's disease can change structural properties (e.g., an alignment of molecules) of a biological tissue, which can be monitored using X-ray diffraction. The physiological or pathological conditions for which the diagnostic indicators described herein can be determined using X-ray diffraction can include diseases of the immune system, diseases of the skin, oncological disease, rheumatic diseases, urological diseases, endocrine diseases, diseases of veins and lymph nodes, diseases of the mammary glands, diseases of respiratory organs, diseases of digestive organs, diseases of heart and blood vessels, diseases of the colon, diseases of the ear, diseases of the throat, and diseases of the nose. For example, an oncological disease can include cancer of the stomach, liver, rectum and colon, esophagus, pancreas, bladder, vagina, lung, oropharynx, nasopharynx, oral mucosa, tongue, skin, brain, thyroid, prostate, breast, cervix, and/or ovary. The diagnostic indicator for assessment of one or more physiological or pathological conditions can be determined by characterizing the changes in the structural properties of a region of skin of a patient (e.g., from the abdomen, between the fingers, or in the thenar web space, which is the space between the index finger and thumb) over time. In some cases, changes of a structure of an extracellular matrix on an organism level in response to morphogenesis in organs allows monitoring of the changes in the extracellular matrix in sites remote from site of morphogenesis. For example, a molecular structure of a biological tissue that is remote from a site of a disease, such as skin on the hand, can be measured to determine a diagnostic indicator for assessment of one or more physiological or pathological conditions, such as cancer of the prostate.

In some embodiments, the methods disclosed herein include determining a diagnostic indicator for assessment of one or more physiological or pathological conditions for a specific patient, including taking into account one or more characteristics of: age, gender, profession, blood pressure, body weight, body-mass index (BMI), cholesterol, cooccurrence of neurological diseases, registration in a cardiodispensary, patient ethnicity, genetic data, and behavioral data, symptoms, reports from the patient, reports of discomfort, reports of chest pain, reports of back pain, reports of shortness of breath, leg swelling, information about chest injury, information about sustained hypertension, reports of constant and severe upper abdominal pain, a metabolic enzyme polymorphism of the patient, a gut microbiota of the patient, a presence of hepatic or renal disease in the patient, and any other information related to the patient.

In some embodiments, the methods disclosed herein include measuring (e.g., in block 110 of method 100 in FIG. 1) a molecular structure of skin that diffracts X-ray light, such as an adipose tissue containing lipids, collagen, a keratin, and/or a glycoprotein.

In some embodiments, more than two measurements of a molecular structure of the region of skin of the patient are taken over time (e.g., in block 220 of method 200). In such cases, in block 220 changes in the molecular structure of the region of skin can be observed using an algorithm to analyze the change in the molecular structure over time (wherein the change can include no change, or no significant change). For example, the algorithm can analyze the measurement data to determine the change in the molecular structure after each successive measurement. The output from the algorithm indicating the change in molecular structure over time can be used to determine the diagnostic indicator for assessment of one or more physiological or pathological conditions. For example, in cases where a series of measurements are taken, the "first time" in method 200 can correspond to the first measurement in the series of measurements, or the "first time" in method 200 can correspond to a measurement other than the first measurement in the series of measurements. Additionally, when a series of measurements are taken, the first time and the second time can be consecutive or nonconsecutive measurements.

In some embodiments, measurements of the molecular structure of the region of skin can be taken at various times (e.g., in block 210 of method 200). The data from the measurements can be analyzed after each successive measurement or at selected intervals using a multi-step algorithm. In some cases, the multi-step algorithm includes statistical analyses to determine the change of the molecular structure of the region of skin in block 220 (e.g., after each measurement). In some cases, more than one measurement can be taken at a particular time (e.g., on the same day, or in a single measurement session), for example, to provide more data for statistical analyses. In some cases, the statistical analyses can include fitting measured data to a function (e.g., a linear function, a polynomial function, an exponential function, or a logarithmic function) to determine the change of the molecular structure of the region of skin. In this process, regression coefficients of the fitted functions can be determined using the statistical analyses. In some cases, comparison of regression coefficients of functions that have been fit to the measured data using multiple measurements can improve the statistical significance of an observed change of the molecular structure of the region of skin over time. In some cases, the statistical analyses may include a determination of a pair-wise distance distribution function, a determination of a Patterson function, a calculation of a Porod invariant, a Fourier transformation, a cluster analysis, a dispersion analysis, a determination of one or more molecular structural periodicities, or any combination thereof. In some cases, the multi-step algorithm can analyze the clustering of data (e.g., derived from the analysis of image data, diffraction data, subject data, or any combination thereof) and re-evaluate observed changes in sample data characteristics and clustering over time. For example, the distance or changes in distance between data points or clusters of data points may be calculated as a function of time. In some instances, the proximity of a new data point to the previous data point(s), or the trajectory of certain data clusters (or the gradient of the trajectory) can describe the observed change in the molecular structure of the region of skin over time. These factors may be used to determine a diagnostic indicator for assessment of one or more physiological or pathological conditions and/or can be interpreted by a physician to determine a diagnostic indicator for assessment of one or more physiological or pathological conditions. Comparing the results of diagnostic indicators for multiple patients can also provide indications of the assessment of one or more physiological or pathological conditions in a patient or in groups of patients.

In some embodiments, the methods disclosed herein include using one or more processors (e.g., a computer workstation) coupled to the X-ray tissue diffractometer to control the X-ray tissue diffractometer. For example, the mechanisms and motors of the X-ray tissue diffractometer, and/or analysis and storage of data from the X-ray tissue diffractometer (e.g., digital image processing, storing and displaying data received from a two-dimensional pixel detector) can be performed using the processor. For example, digital image processing can include discrete two-dimensional Fourier transform of images, image segmentation, definition of descriptors of boundaries and regions, and/or recognition of objects within one or more images. The processor(s) can also be coupled to memory, and can be local to the X-ray tissue diffractometer or can be in the cloud, as described further herein.

In some embodiments, the methods disclosed herein include controlling one or more X-ray tissue diffractometers performing the non-invasive characterization of the region of skin of the patient using a processor. The method can further include digital image processing of one or more images related to the molecular structure of the region of skin which can also be performed using the processor. For example, the digital image processing of images (e.g., images containing X-ray diffraction data) can include one or more of: producing a discrete two-dimensional Fourier transform of one or more images, performing image segmentation of the one or more images, defining descriptors of boundaries or regions in the one or more images, and recognizing objects in the one or more images. The method can further include storing and displaying data received from the X-ray tissue diffractometer.

X-ray diffraction (XRD) using a tissue diffractometer is an example of a "non-invasive observation" or "non-invasive biological tissue characterization" of a patient because it does not include the introduction of instruments into the body of a patient. Non-invasive observation or characterization can advantageously spare the patient from pain.

Figure 3A:
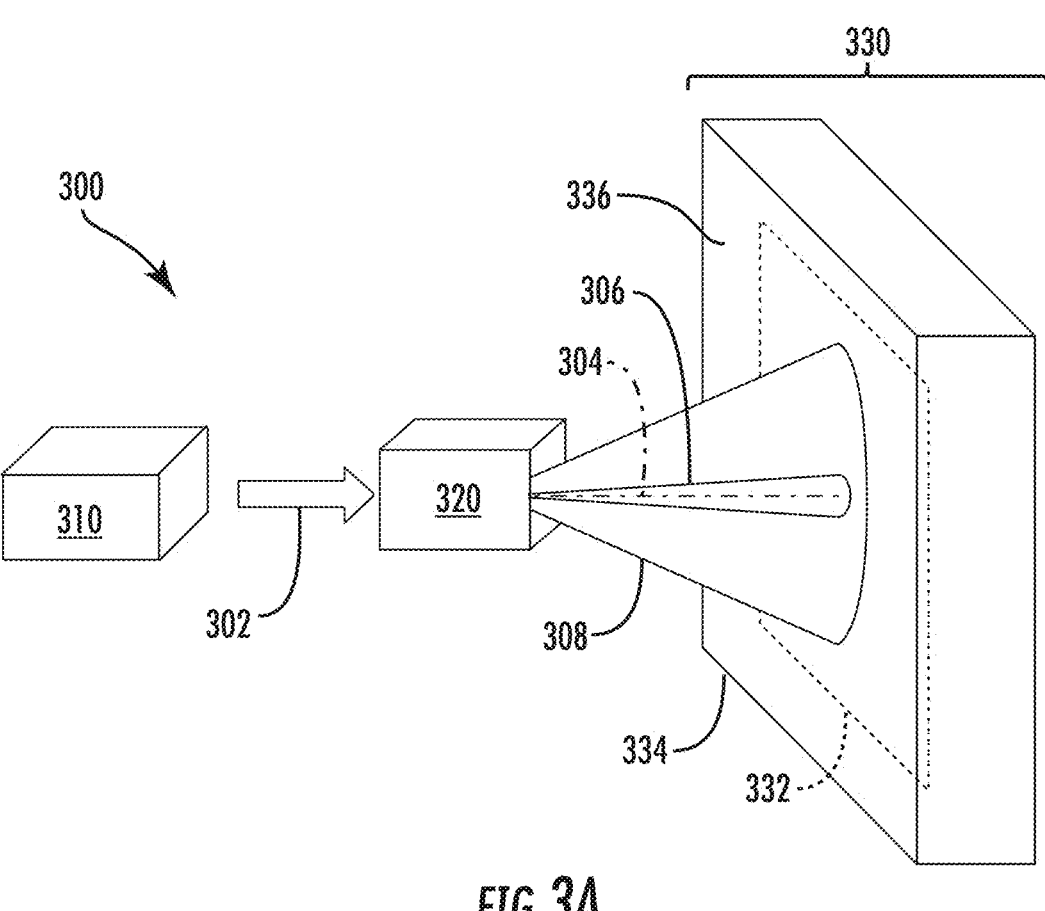
FIG. 3A shows a simplified schematic of an example of an X-ray tissue diffractometer in a perspective view, in accordance with some embodiments.
Figure 3B:
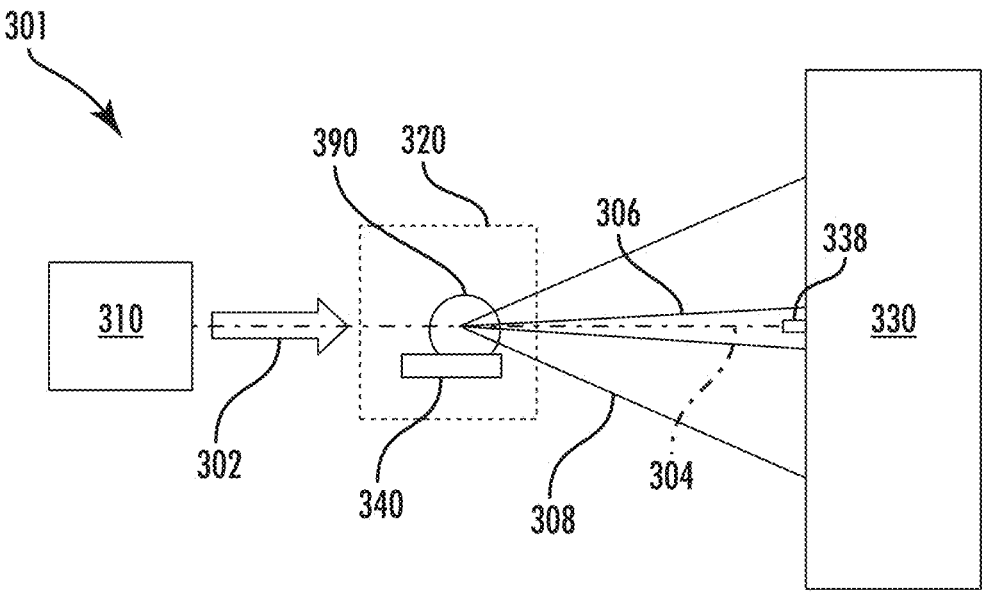
FIG. 3B shows another simplified schematic of an example of an X-ray tissue diffractometer in a side view including a fixture for a biological tissue sample, in accordance with some embodiments.
Figure 3C:
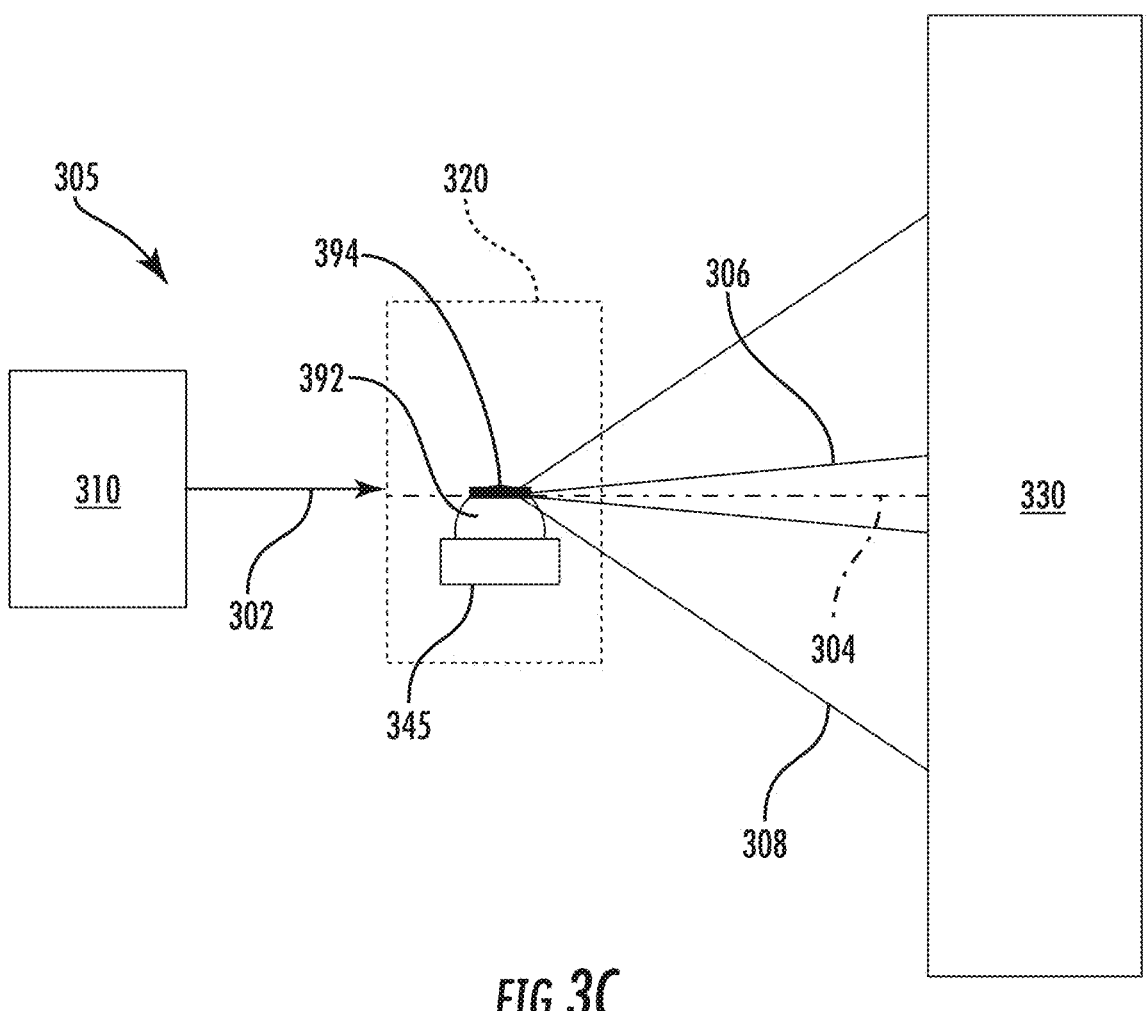
FIG. 3C shows another simplified schematic of an example of an X-ray tissue diffractometer in a side view for grazing incidence X-ray diffraction of a biological tissue sample, in accordance with some embodiments.

FIGS. 3A-3C show simplified schematics of examples of X-ray tissue diffractometers that can be used to perform the methods disclosed herein, in accordance with some embodiments.

FIG. 3A shows a simplified schematic of an example of an X-ray tissue diffractometer 300 in a perspective view, in accordance with some embodiments. X-ray tissue diffractometer 300 includes: a positioning area 320 for the biological tissue, an X-ray source 310, and an X-ray receiver 330. The X-ray source 310 provides a primary incident beam of X-rays 302 directed at the biological tissue to be analyzed (the biological tissue being held in positioning area 320). The biological tissue can include a region of skin of a patient, and the positioning area 320 can include a fixture to position the region of skin in the correct position, as described herein. The measurement of the biological tissue (e.g., skin) can be done in vivo and/or in vitro to determine a diagnostic indicator for assessment of one or more physiological or pathological conditions. The X-ray receiver 330 can include a two-dimensional pixel detector 332 designed to detect the transmitted micro-beam of X-rays 304 passed through the analyzed biological tissue as well as part or all X-rays 306 and 308 that are diffracted by the biological tissue. X-rays 306 are small-angle x-ray scattering (SAXS) signals, and X-rays 308 are wide-angle x-ray scattering (WAXS) signals, both of which can be detected using X-ray receiver 330. In some cases, the two-dimensional pixel detector 332 can be inside a protection container 334 that contains a vacuum (or low pressure) environment or is filled with an inert gas (e.g., neon or helium), and includes a window or wall 336 facing the biological tissue that is substantially transparent to X-rays. X-ray receiver 330 can also include a crystal-analyzer comprising a rotary mechanism comprising piezoelectric elements in some cases. The X-ray tissue diffractometer 300 can also include a filter in front of the two-dimensional pixel detector 332 in some cases. For example, the filter can be positioned to screen the two-dimensional pixel detector 332 from a transmitted portion of the X-rays 304, and/or the filter at least partially reduces an intensity of the transmitted portion of the X-rays 304.

The X-ray source 310 of FIG. 3A can include a radiation source operating in continuous mode, a beam shaping apparatus (e.g., a mirror, and/or an apparatus forming X-ray micro-beam), at least one monochromator, and at least one collimating and focusing optical device. X-ray source 310 can include components such that incident X-rays 302 are substantially collimated, substantially monochromatic, substantially monoenergetic, and/or have a rectangular or circular cross-section. For example, X-ray source 310 can include one or more of a collimating aperture, one or more monochromators (e.g., a highly ordered pyrolytic graphite (HOPG) monochromator, and/or a multilayer monochromator), and a beam forming apparatus comprising a Kratki or Montel mirror collimator. In some cases, the X-ray source 310 includes a parabolic shaped multilayer mirror that converts divergent X-rays into collimated parallel X-rays.

FIG. 3B shows another simplified schematic of an example of an X-ray tissue diffractometer 301 in a side view including a fixture 340 for a biological tissue sample 390, in accordance with some embodiments. X-ray tissue diffractometer 301 is similar to X-ray tissue diffractometer 300 in FIG. 3A, and shares some of the same components. The positioning area 320 in this example incudes a fixture 340 which positions a biological tissue sample 390 (e.g., an in vivo or in vitro sample containing skin of a patient) in a position that is mechanically or geometrically aligned with the X-ray source 310 and the X-ray receiver 330. The fixture 340 is advantageous because the intensity of the diffracted X-rays 306 and/or 308 can be increased by aligning the tissue sample with the X-ray source 310 and the X-ray receiver 330. For example, as described further herein, the fixture can be configured to align a sample of skin between the fingers or of the thenar web space of a patient with the X-ray source 310 and the X-ray receiver 330 to perform SAXS or WAXS X-ray diffraction measurements. In another example, as described further herein, the fixture can be configured to align a sample of skin between the fingers or of the thenar web space of a patient with the X-ray source 310 and the X-ray receiver 330 to perform grazing incidence X-ray diffraction measurements.

The X-ray tissue diffractometer 301 in FIG. 3B also includes filter 338, which is positioned in front of the two-dimensional pixel detector of the receiver 330. Filter 338 is positioned to screen the two-dimensional pixel detector of receiver 330 from transmitted portion of X-rays 304, and/or at least partially reduce an intensity of the transmitted portion of the X-rays 304.

FIG. 3C shows another simplified schematic of an example of an X-ray tissue diffractometer 305 in a side view for grazing incidence X-ray diffraction of a biological tissue sample 392, in accordance with some embodiments. X-ray tissue diffractometer 305 is similar to X-ray tissue diffractometer 300 in FIG. 3A and to X-ray tissue diffractometer 301 FIG. 3B, and shares some of the same components. The positioning area 320 in this example incudes a fixture 345 which positions a surface 394 of a biological tissue sample 392 in a position that is mechanically or geometrically aligned with the X-ray source 310 and the X-ray receiver 330 such that grazing incidence X-ray diffraction can be performed on surface 394. In other words, fixture 345 can position sample 392 such that a relative position and orientation between the incident X-rays 302 and a surface 394 of the sample 392 is configured for grazing incidence X-ray diffraction. For example, biological tissue sample 392 can include skin on its surface 394. In some cases, the angle between the incident X-rays 302 and the surface 394 of the biological tissue sample 392 in a grazing incidence X-ray diffraction measurement is less than 10 degrees, or less than 5 degrees, or less than 2 degrees. The fixture 345 can be advantageous because X-rays are absorbed when moving through material, and grazing incidence X-ray diffraction preferentially measures material that is close to the exposed surface 394. Therefore, the intensity of the diffracted X-rays 306 and/or 308 from the portion of sample 392 that includes skin can be increased by aligning the surface 394 of the tissue sample 392 with the X-ray source 310 and the X-ray receiver 330.

Figure 4:
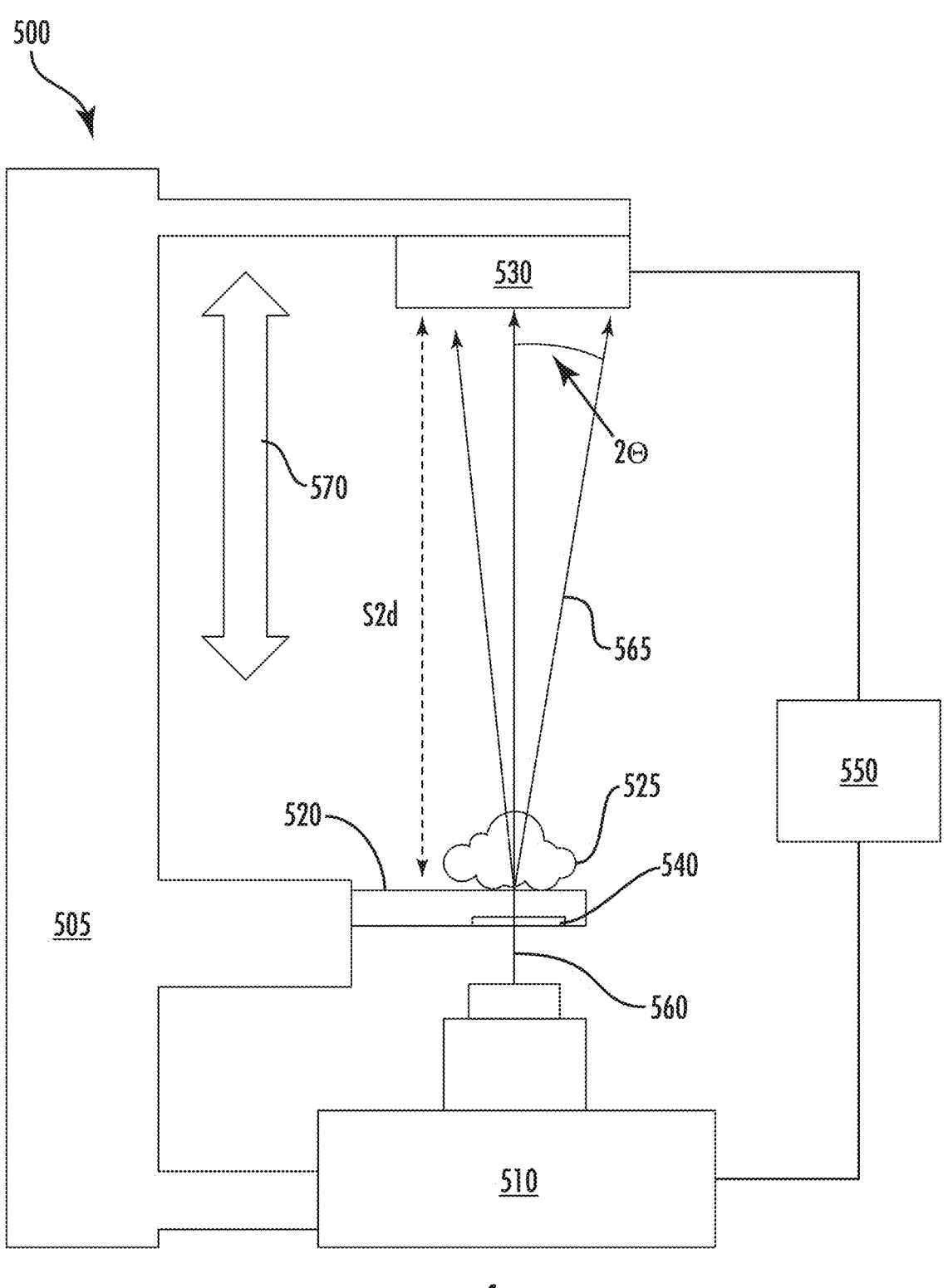
FIG. 4 is a schematic diagram of a system including measurement equipment that is a tissue diffractometer, in accordance with some embodiments.

FIG. 4 is a schematic diagram of a system including measurement equipment that is a tissue diffractometer, in accordance with some embodiments. The tissue diffractometer of system 500 was used to experimentally measure X-ray diffraction (XRD) data of biological tissue samples including skin of mice, as described further in Example 1. Tissue diffractometer is coupled to processor 550, which can control the tissue diffractometer of system 500 and save and analyze the XRD data from the tissue diffractometer. The tissue diffractometer includes an X-ray source 510, which emits X-rays 560. The X-rays can be diffracted by biological tissue sample 525, which is positioned in a measurement region using a fixture 520. The diffracted X-rays 565 can then be detected using an X-ray receiver 530, which can include a coordinate-sensitive digital detector of X-rays. The X-ray source 510, the fixture 520 and the X-ray receiver 530 can be coupled to a rigid frame 505 to align the components with one another. The rigid frame 505 can also be adjustable in some cases, to move in direction 570, and change the distance S2d from the sample 525 to the X-ray receiver 530. For example, the distance S2d could be adjusted from 20 mm for WAXS measurements to 160 mm for SAXS measurements. The X-ray receiver 530 is electrically coupled to a processor 550, or to a set of processors locally and/or in the cloud, which are used to analyze the data. For example, the processor 550 can plot an X-ray intensity versus q value (derived from the S2d and the diffraction angle 2θ). The processor 550 can also be coupled to the X-ray source 510 to control it.

Figures 5A, 5B:
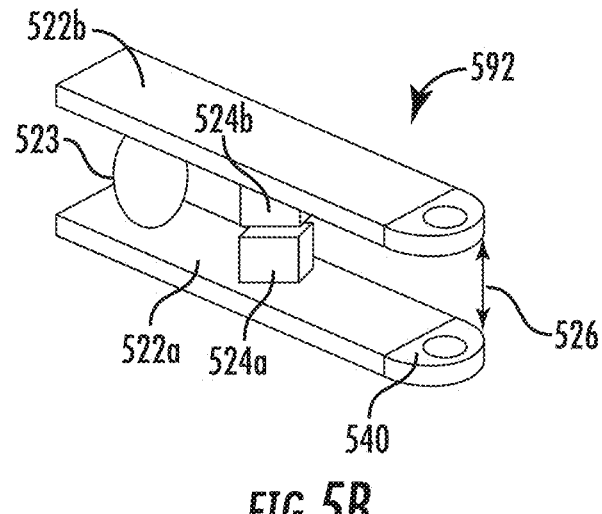
FIG. 5A is a schematic diagram of an X-ray tissue diffractometer, in accordance with some embodiments.
FIG. 5B also shows a schematic of a fixture of the X-ray diffractometer in FIG. 5A, in accordance with some embodiments.

FIG. 5A is a schematic diagram of an X-ray tissue diffractometer 501, in accordance with some embodiments. X-ray tissue diffractometer 501 is similar to X-ray tissue diffractometer 500 in FIG. 4, and shares some of the same components. FIG. 5B also shows a schematic of fixture 592 of X-ray diffractometer 501, in accordance with some embodiments. Fixture 592 includes a clamping mechanism with an incident-side part 522a and an exit-side part 522b coupled to a pivot mechanism 523. For example, pivot mechanism 523 can be a hinge or a spring (like in a clothespin). In some cases, pivot mechanism is a hinge or a ball joint and there is a separate spring or elastic material providing a clamping force to close the incident-side part 522a and the exit-side part 522b together. The fixture 592 also includes stops 524a and 524b, which form a consistent spacing 526 when the fixture 592 is closed. In some embodiments, the biological tissue sample 525 includes a skin web between the fingers, or skin of the thenar web space between the thumb and index finger, and the fixture 592 has dimensions to accommodate those regions of skin of a patient. For example, spacing 526 can be from about 0.5 mm to 5 mm, or from 1 mm to 3 mm. The biological tissue sample 525 can be clamped by the incident-side part 522a and the exit-side part 522b to be held in place for an XRD measurement where the incident X-rays 560 pass through a collimating aperture 540, and through a first window 527a of fixture 592, before interacting with the sample 525. The diffracted X-rays 565 also pass through a second window 527b of fixture 592 before being detected by the X-ray receiver 530. Window 527a and 527b can be made of a material that is substantially transparent to X-rays, such as a thermoplastic material (e.g., polymethyl methacrylate, polycarbonate), a carbon fiber composite material, or beryllium. The X-ray receiver can be movable in a direction 570 which is approximately parallel with the incident X-rays 560 to change the distance between the sample 525 and the X-ray receiver 530.

Figure 5C:
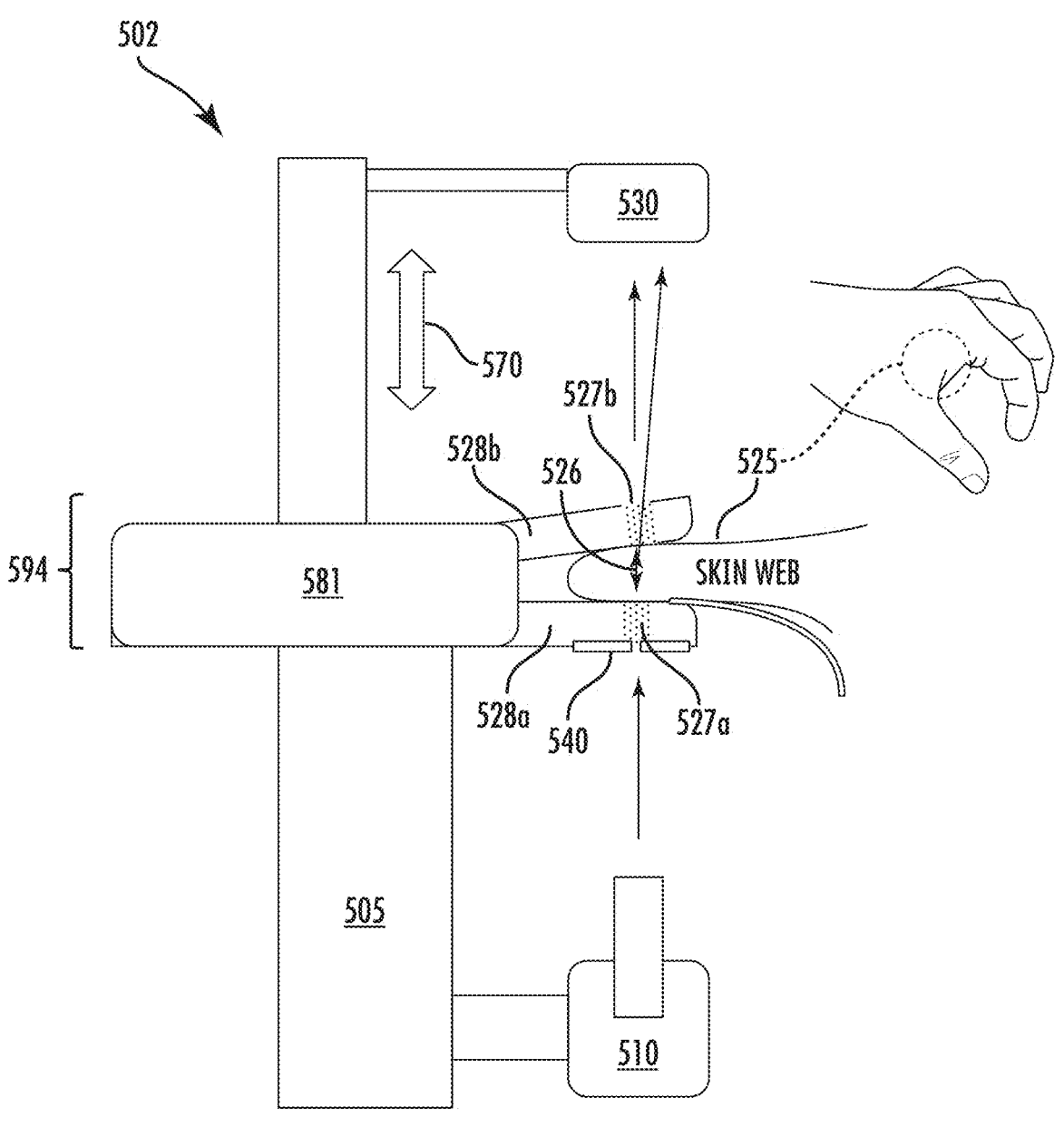
FIG. 5C is a schematic diagram of an X-ray tissue diffractometer, in accordance with some embodiments.

FIG. 5C is a schematic diagram of an X-ray tissue diffractometer 502, in accordance with some embodiments. X-ray tissue diffractometer 501 is similar to X-ray tissue diffractometer 500 in FIG. 4 and to X-ray tissue diffractometer 501 in FIGS. 5A and 5B, and shares some of the same components. In this example, X-ray diffractometer 502 includes fixture 594. Fixture 594 includes a fixed wedge configuration with a incident-side part 528a and an exit-side part 528b coupled to a block 581. Incident-side part 528a and an exit-side part 528b coupled to a block 581 are rigidly coupled in this example and form a consistent spacing 526 for the X-rays to interact with during an XRD measurement. In some embodiments, the biological tissue sample 525 includes a skin web between the fingers, or skin of the thenar web space between the thumb and index finger, and the fixture 592 has dimensions to accommodate those regions of skin of a patient. For example, spacing 526 can be from about 0.5 mm to 5 mm, or from 1 mm to 3 mm. The biological tissue sample 525 can be held in place for an XRD measurement where the incident X-rays pass through a collimating aperture 540, and through a first window 527a of fixture 594, before interacting with the sample 525. The diffracted X-rays also pass through a second window 527b of fixture 594 before being detected by the X-ray receiver 530. The X-ray receiver can be movable in a direction 570 which is approximately parallel with the incident X-rays 560 to change the distance between the sample 525 and the X-ray receiver 530.

Figure 5D:
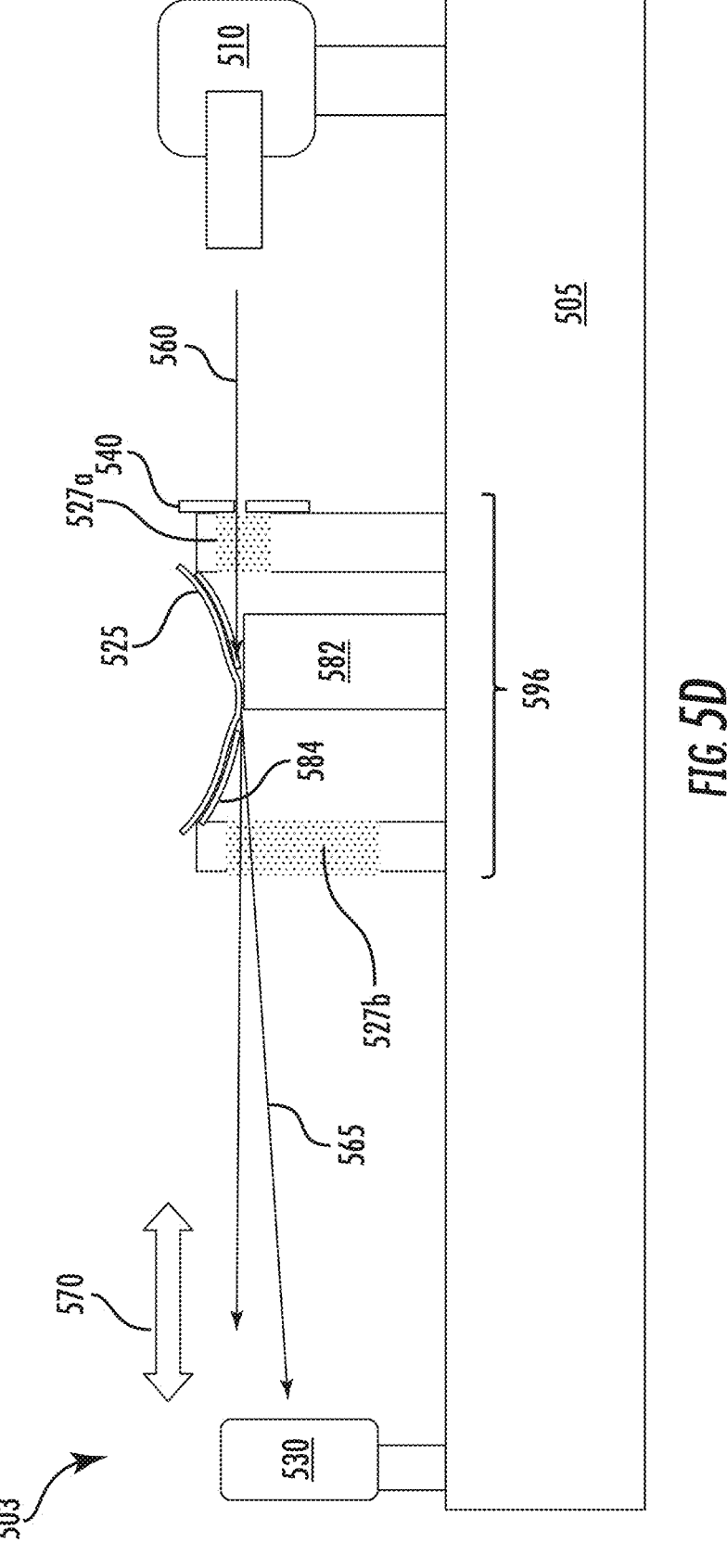
FIG. 5D is a schematic diagram of an X-ray tissue diffractometer, in accordance with some embodiments.

FIG. 5D is a schematic diagram of an X-ray tissue diffractometer 503, in accordance with some embodiments. X-ray tissue diffractometer 503 is similar to X-ray tissue diffractometer 500 in FIG. 4, to X-ray tissue diffractometer 501 in FIGS. 5A and 5B, and to X-ray tissue diffractometer 502 in FIG. 5C, and shares some of the same components. In this example, X-ray diffractometer 503 includes fixture 596, which positions a biological tissue sample 525 including skin of a patient such that a surface of the sample 525 is aligned for grazing incidence X-ray diffraction (e.g., as described with respect to tissue diffractometer 305 in FIG. 3C).

Fixture 596 includes a block stop 582 with a flat surface approximately parallel with the incident X-rays 560, that is located adjacent to the measurement region. Block stop 582 can cause the sample 525 to have a locally flat surface (since the tissue sample is deformable it will conform to the flat surface of the block stop 582) to interact with the incident X-rays 560 in a grazing incidence geometry. The angle between the surface of the block stop 582 forming the surface of the sample 525 and the incident X-rays 560 can be less than 10 degrees, or less than 5 degrees, or less than 2 degrees. In some cases, the relative alignment between the block stop 582 and the incident X-rays 560 can be fixed or adjustable, for example by coupling the block stop 582 to the frame 505 using a pivotable or rotatable mount. The biological tissue sample 525 that can be measured using the fixture 596 includes skin from various parts of the body, such as from the hands, arms, feet, legs, etc. Fixture 596 can include a curved surface 584 with an opening to allow the skin of the sample 252 to penetrate into the X-ray beam path. The biological tissue sample 525 can be held in place for a grazing incidence XRD measurement where the incident X-rays 560 pass through a collimating aperture 540, and through a first window 527a of fixture 596, before interacting with the sample 525 in a measurement region. The diffracted X-rays also pass through a second window 527b of fixture 596 before being detected by the X-ray receiver 530. The X-ray receiver can be movable in a direction 570 which is approximately parallel with the incident X-rays 560 to change the distance between the sample 525 and the X-ray receiver 530.

Figure 6:
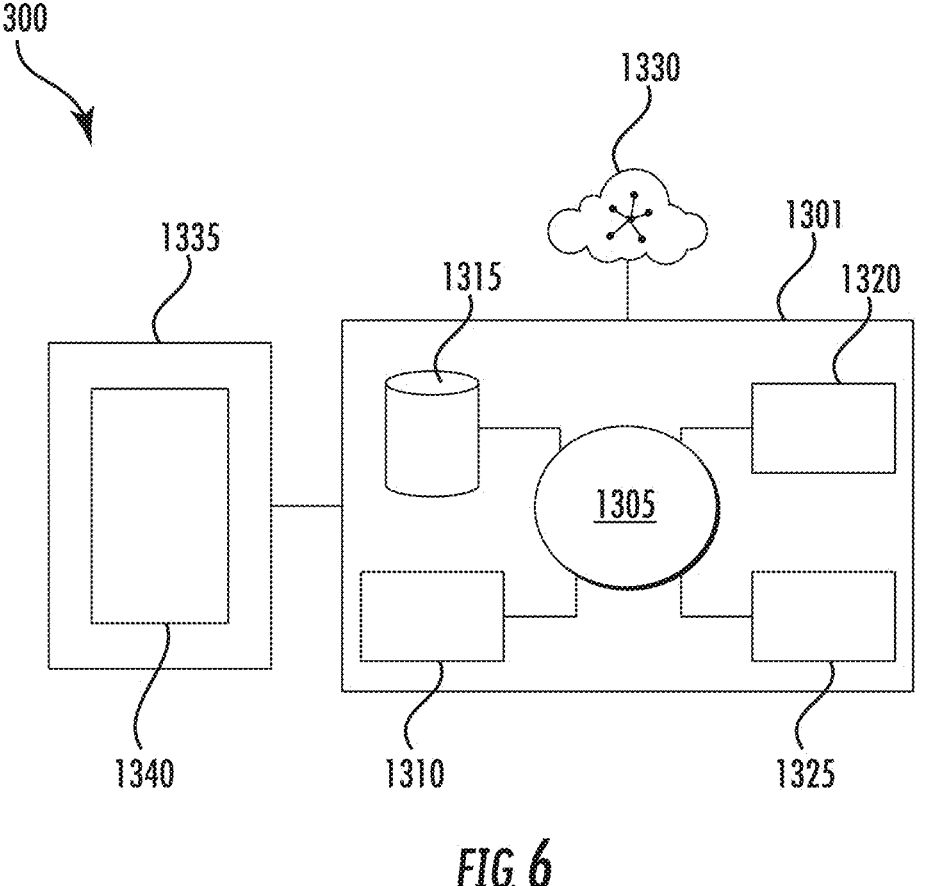
FIG. 6 shows a system including a computer system, a network, and an electronic display, in accordance with some embodiments.

The present disclosure provides computer systems that are programmed to implement methods of the disclosure. FIG. 6 shows a system 1300 including a computer system 1301, a network 1330, and an electronic display 1335, in accordance with some embodiments. The computer system 1301 is programmed or otherwise configured to implement methods described herein (e.g., obtaining data from measurement equipment, processing the data, etc.). The computer system 1301 can regulate various aspects of the present disclosure, such as controlling measurement equipment, and processing global data, local measurement data, patient data, or any combination thereof. The computer system 1301 can be an electronic device of a user or a computer system that is remotely located with respect to the electronic device. The electronic device can be a mobile electronic device. The computer system 1301 may be a post-classical computer system (e.g., a quantum computing system).

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

Methods and systems of the present disclosure can be implemented by way of one or more algorithms. An algorithm can be implemented by way of software upon execution by the CPU 1305. The algorithm can, for example, be a machine learning algorithm as described herein.

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user (e.g., a cloud server). Examples of remote computer systems include personal computers (e.g., portable PC), slate or tablet PCs (e.g., Apple® iPad, Samsung® Galaxy Tab), telephones, smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine-readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processor adapted to execute the code, or can be compiled during runtime. The code can be supplied in a programming language that can be selected to enable the code to execute in a precompiled or as-compiled fashion.

Some aspects of the systems and methods provided herein, such as the computer system 1301, can be embodied in programming. Some aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory), or on a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the databases and the processes described herein. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, an interface for a healthcare worker or an individual patient to upload local measurement data, patient data, or any combination thereof to a computer database. The UI can also provide an interface for a healthcare worker or an individual patient to view local measurement data, patient data, or any combination thereof. Examples of UI's include, without limitation, a graphical user interface (GUI) and web-based user interface.

Example 1

In this example, mice were inoculated with prostate cancer, and X-ray diffraction (XRD) data was measured over time to observe changes in the XRD measurement data compared to a control group of mice that were not inoculated. The XRD measurements were performed in vitro on samples including the skin of the abdomen of the mice and included both SAXS and WAXS measurements.

FIG. 4 is a schematic diagram of a system including the measurement equipment that was used in this example. The measurement equipment included a tissue diffractometer, which was used to measure the XRD measurement data from the mice. The tissue diffractometer was controlled by a processor, and a processor was used to save and analyze the data. The tissue diffractometer included an X-ray source 510, which emitted X-rays 560 and were diffracted by biological tissue sample 525, which was positioned in a measurement region using a fixture 520. The diffracted X-rays 565 were detected using an X-ray receiver 530, which included a coordinate-sensitive digital detector of X-rays. The X-ray source 510, the fixture 520 and the X-ray receiver 530 were coupled to a rigid frame 505 to align the components with one another, and the rigid frame 505 was adjustable such that it could move in direction 570. The distance S2d from the sample 525 to the X-ray receiver 530 was adjusted from 20 mm for WAXS measurements to 160 mm for SAXS measurements in this Example. The X-ray receiver 530 was also electrically coupled to a processor 550, which analyzed the data, for example to plot an X-ray intensity versus q value (derived from the S2d and the diffraction angle 2θ).

In this example, the XRD measurements were performed at two sample-to-detector distances (S2d), 20 mm and 160 mm. The measurements were performed on the control group of mice, and on groups of inoculated mice after 2 days, 4 days, and 16 days.

Figure 7A:
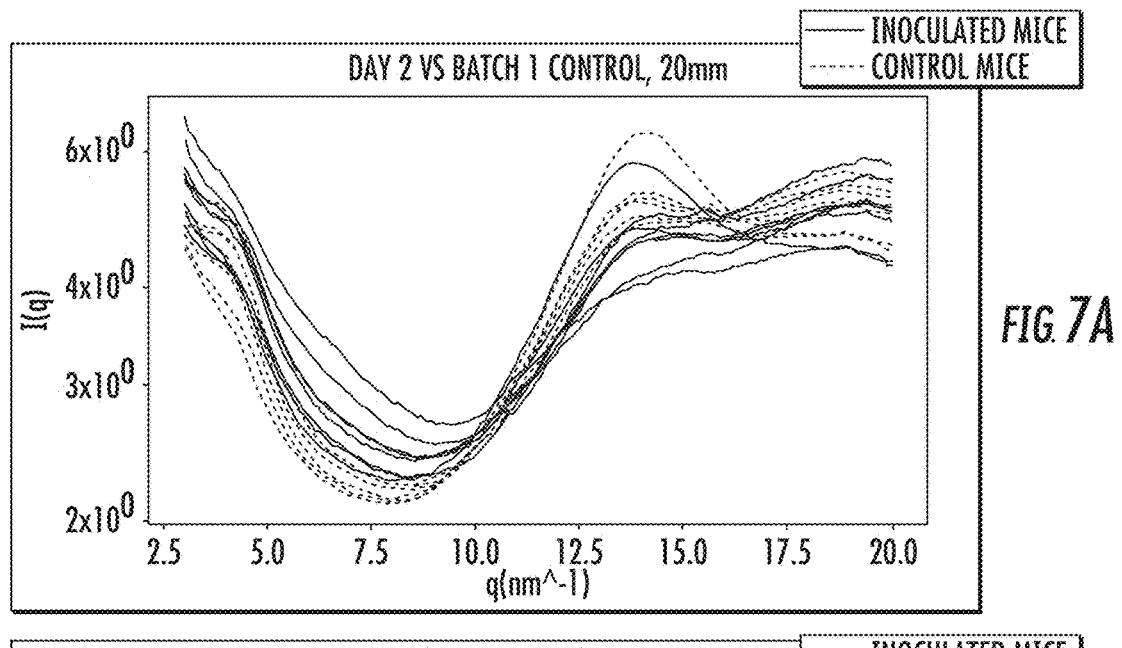
FIGS. 7A-7C show examples of normalized wide angle X-ray scattering (WAXS) X-ray diffraction (XRD) data from inoculated groups compared to a control group after 2 days, 4 days, and 16 days, respectively.
Figure 7B:
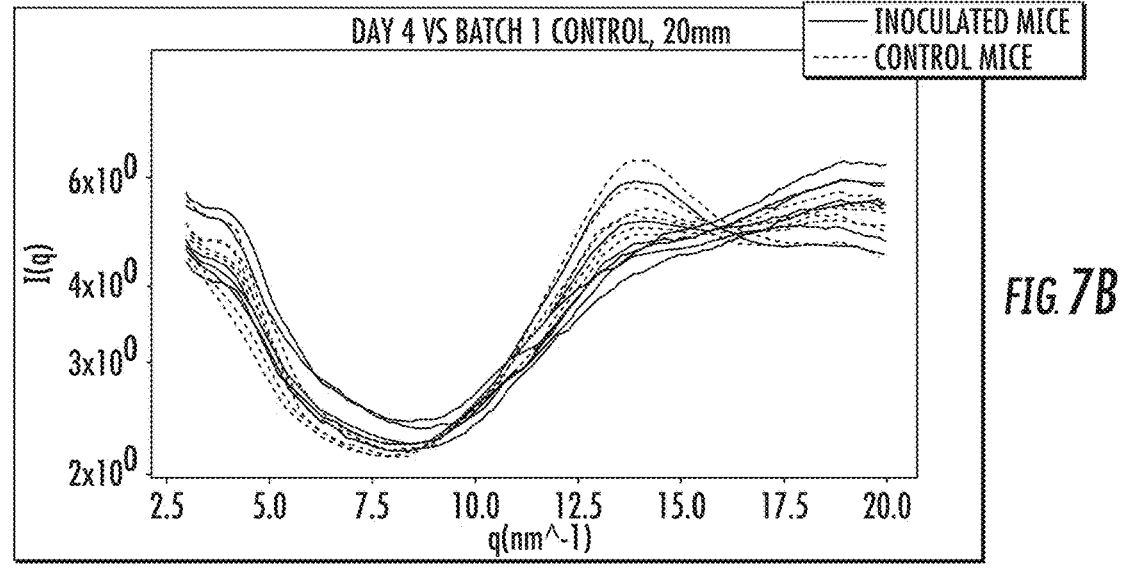
Figure 7C:
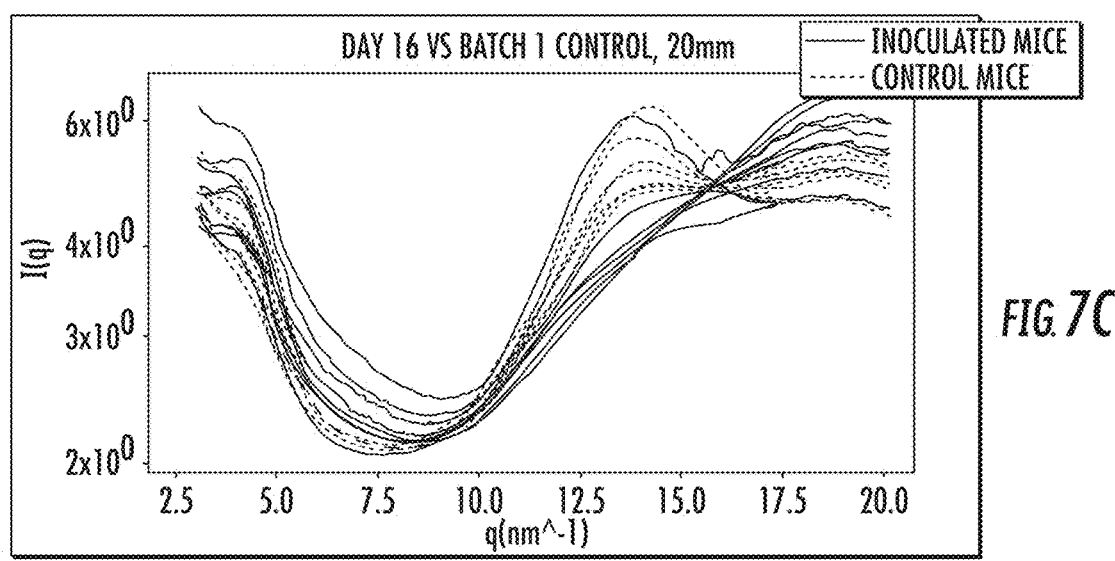

FIGS. 7A-7C show examples of normalized WAXS XRD data from the inoculated groups compared to the control group after 2 days, 4 days, and 16 days, respectively. The sample to detector distances (S2d) were 20 mm for these WAXS measurements. The XRD data from the control group all show a pronounced peak at a q of about 13.5 nm$^{-1}$, where the d-spacing (d) between diffraction planes is related to q by the expression d=2π/q.

Figure 7D:
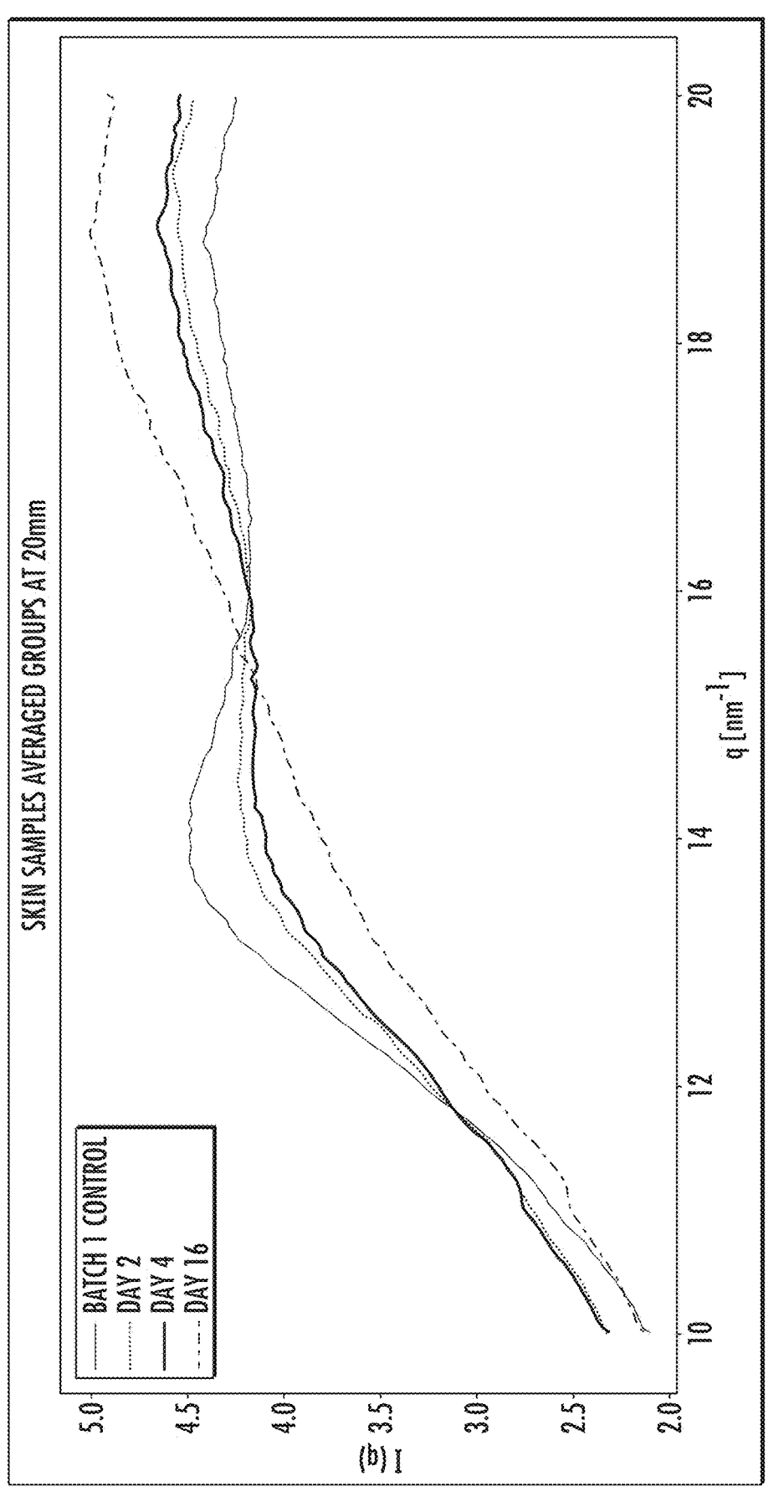
FIG. 7D shows the XRD measurement data from FIGS. 7A-7C, where the multiple XRD measurements shown in each of FIGS. 7A-7C were averaged for the control group and the inoculated groups after 2 days, 4 days, and 16 days.

FIG. 7D shows the XRD measurement data from FIGS. 7A-7C, where the multiple XRD measurements shown in each of FIGS. 7A-7C were averaged for the control group and the inoculated groups after 2 days, 4 days, and 16 days. The XRD measurement data from the inoculated groups shows a decrease in the 13.5 nm$^{-1}$ peak over time, and an increase in intensity of a broad XRD peak at a q of about 19 nm$^{-1}$.

FIGS. 8A-8D show further analyses of the averaged XRD measurement data of FIG. 7D. The x-axes in the plots in FIGS. 8A-8D are days since inoculation, and the y-axes relate to features of the XRD peaks shown in FIG. 7D. Each of the XRD data curves in FIG. 7D was fit using Gaussian peaks, and an amplitude and full-width at half maximum (FWHM) for each Gaussian peak was determined. FIGS. 8A-8D plot the amplitude and the standard deviation of the fit Gaussian peaks of the XRD data in FIG. 7D (at 13.5 nm$^{-1}$ and 19 nm$^{-1}$) for the control group (Day 0) and for the inoculated groups over time (Days 2, 4, and 16). The time-series trajectory data in each plot was then fit using a piecewise cubic Hermite interpolating polynomial (PCHIP), which was used to preserve monotonicity in the interpolation of the data and to avoid overshooting. Therefore, FIGS. 8A-8D show an example of how the normalized XRD measurement data can be analyzed. In this case, the normalized XRD measurement data was averaged, fit with Gaussian peaks, parameters of the Gaussian peaks (e.g., amplitude and FWHM) were plotted, and the plotted parameters were fit with a function (e.g., a PCHIP in this example, or other polynomials may be used in further examples).

Figure 8A:
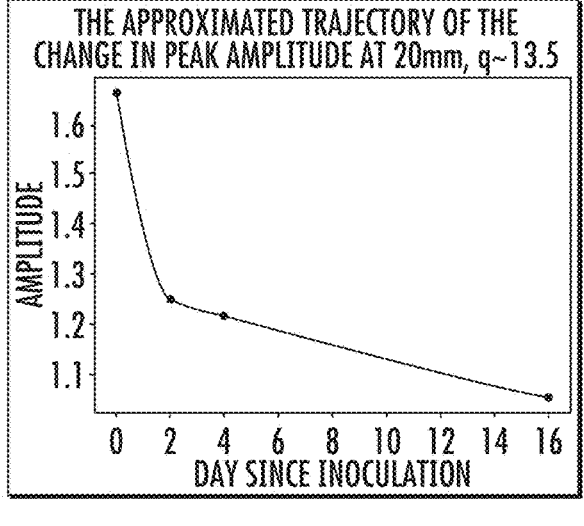
FIGS. 8A-8D show further analyses of the averaged XRD measurement data of FIG. 7D.

FIG. 8A shows the amplitude of the Gaussian peaks centered at about 13.5 nm$^{-1}$ over time for the control group (Day 0) and the inoculated groups (Day 2, 4, and 16). This analyzed XRD data shows that the amplitude of the Gaussian peaks centered at about 13.5 nm$^{-1}$ decreased over time for the inoculated groups.

Figure 8B:
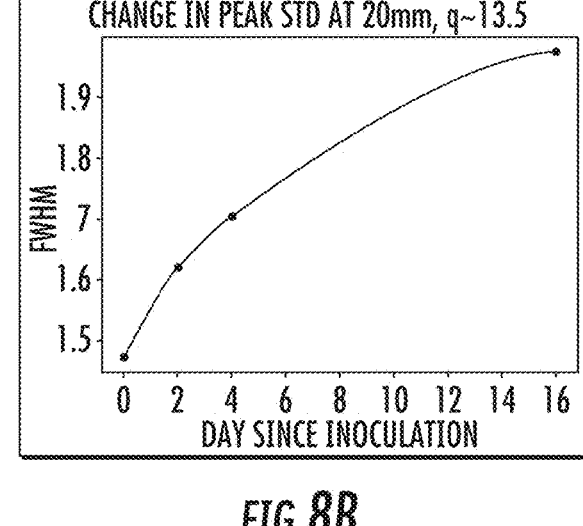

FIG. 8B shows the FWHM of the Gaussian peaks centered at about 13.5 nm$^{-1}$ over time for the control group (Day 0) and the inoculated groups (Day 2, 4, and 16). This analyzed XRD data shows that the FWHM of the Gaussian peaks centered at about 13.5 nm$^{-1}$ increased over time for the inoculated groups.

Figure 8C:
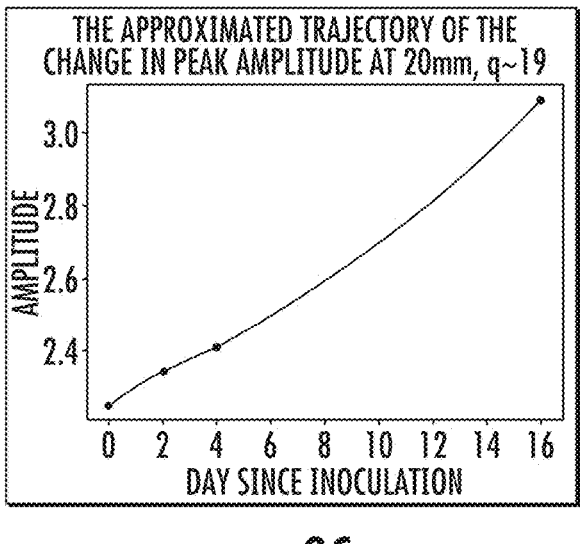

FIG. 8C shows the amplitude of the Gaussian peaks centered at about 19 nm$^{-1}$ over time for the control group (Day 0) and the inoculated groups (Day 2, 4, and 16). This analyzed XRD data shows that the amplitude of the Gaussian peaks centered at about 19 nm$^{-1}$ increased over time for the inoculated groups.

Figure 8D:
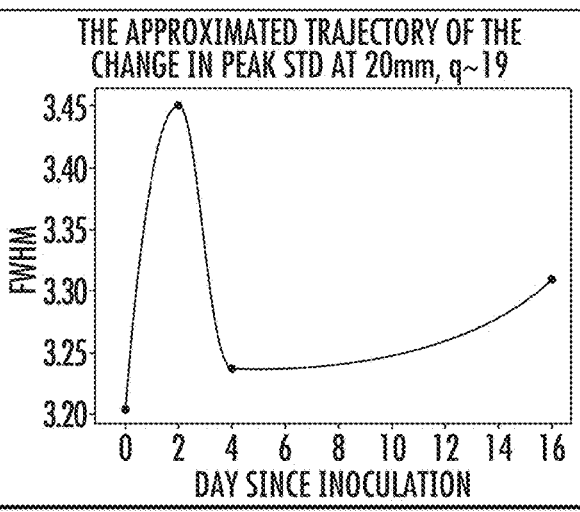

FIG. 8D shows the FWHM of the Gaussian peaks centered at about 19 nm$^{-1}$ over time for the control group (Day 0) and the inoculated groups (Day 2, 4, and 16). This analyzed XRD data shows a less clear trend than the XRD data in FIG. 8B. The data may indicate that the FWHM of the Gaussian peaks centered at about 19 nm$^{-1}$ increased over time for the inoculated groups compared to the control group (Day 0).

Figure 8E:
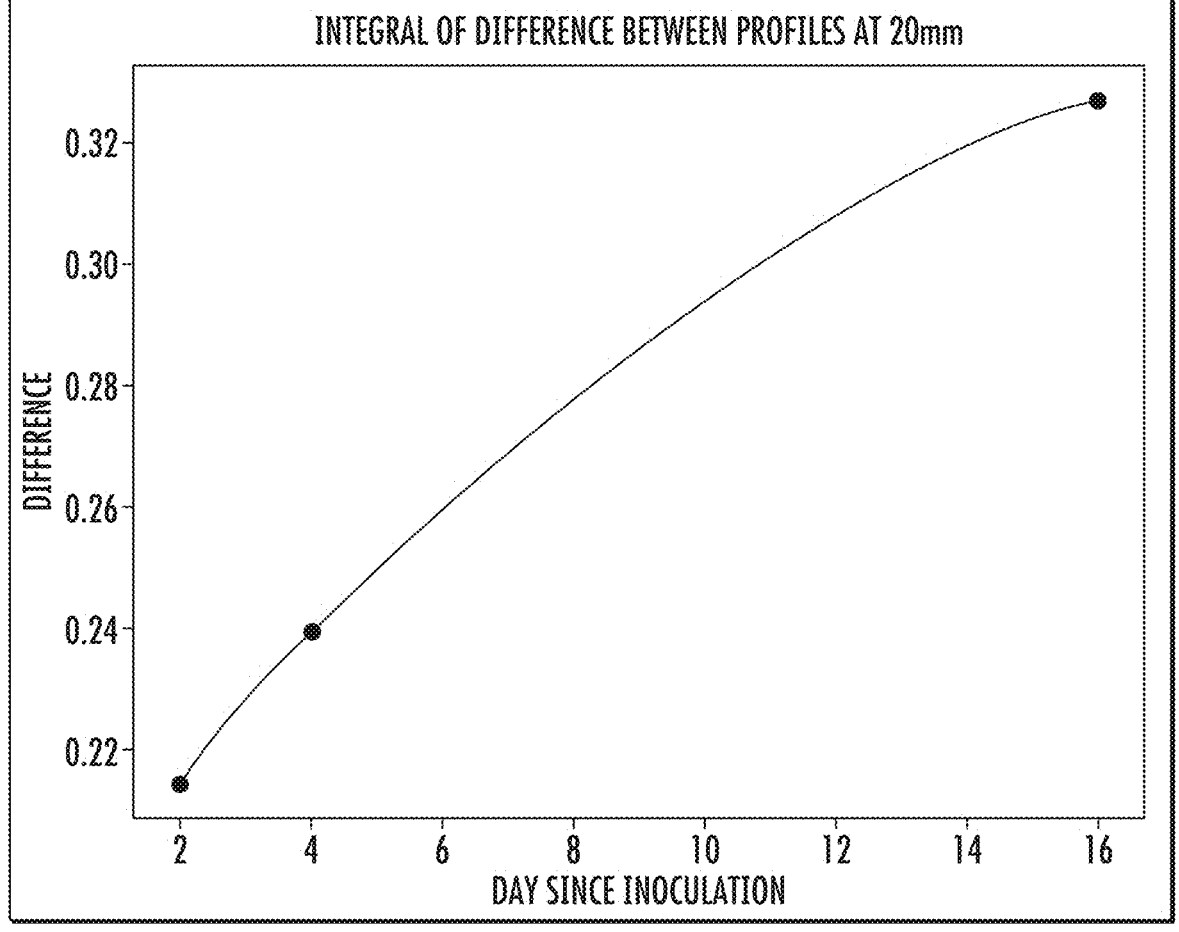
FIG. 8E shows another type of analysis of the averaged XRD measurement data of FIG. 7D.

FIG. 8E shows another type of analysis of the averaged XRD measurement data of FIG. 7. The curves from the control group were subtracted from each of the curves of the inoculated groups, and then an integral of the difference between the curves was taken over the q range of 10 nm$^{-1}$ to 20 nm$^{-1}$. In other words, the data in FIG. 7D was analyzed to determine a difference in total normalized intensity between the XRD measurements of the control group and the inoculated groups over time (for the q range from 10 nm$^{-1}$ to 20 nm$^{-1}$). This procedure was done for the data after 2 days, 4 days, and 16 days to determine the difference in total normalized intensity between the XRD measurements of the control group and the inoculated groups over time. The analyzed data in FIG. 8E shows that the difference in XRD measurement data intensity between the inoculated groups and the control group increased over time (in a q range from 10 nm$^{-1}$ to 20 nm$^{-1}$).

Figures 9A, 9B, 9C:
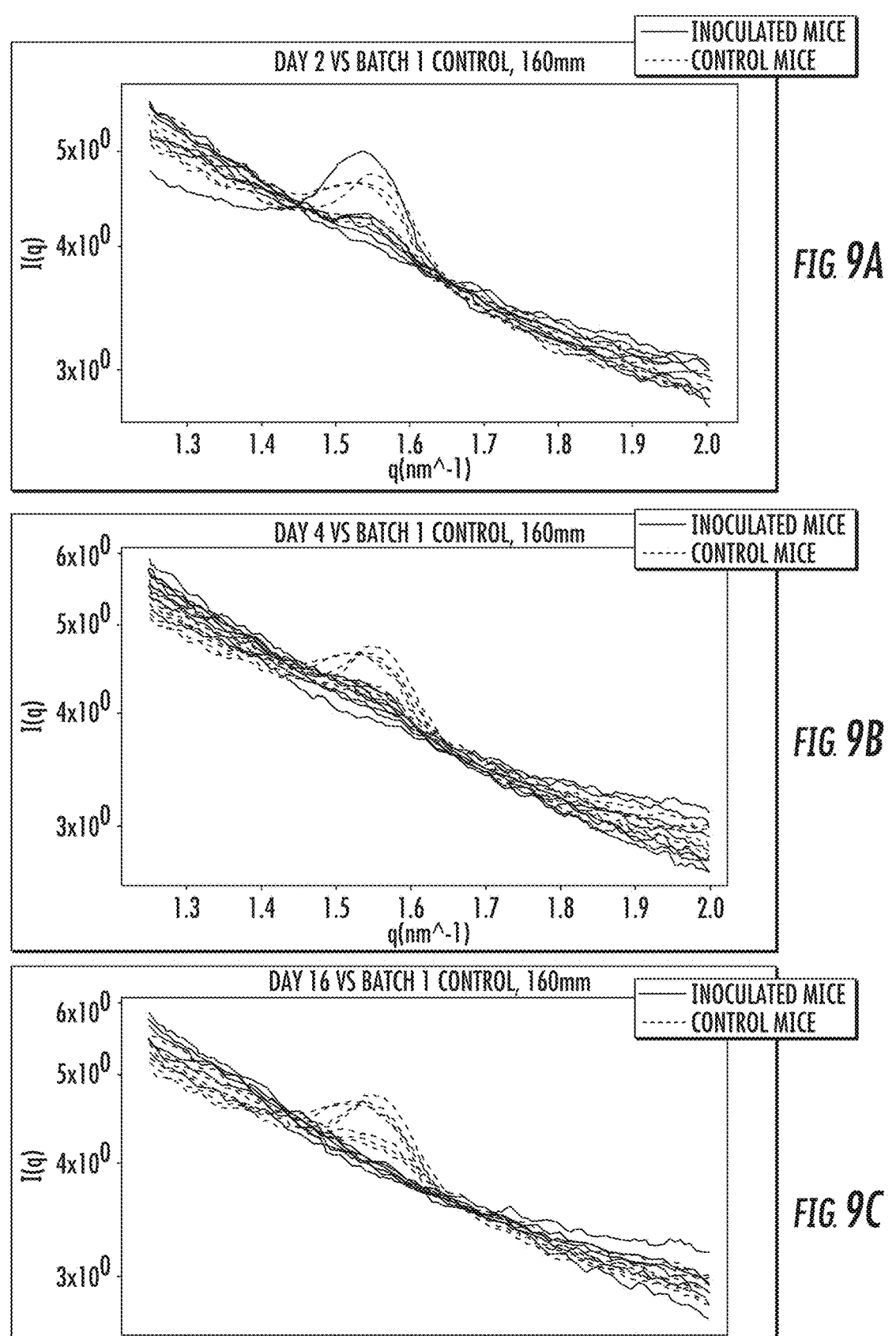
FIGS. 9A-9C show examples of normalized small angle X-ray scattering (SAXS) XRD measurement data from the inoculated groups compared to the control group after 2 days, 4 days, and 16 days, respectively, with a sample to detector distance (S2d) of 160 mm.

FIGS. 9A-9C show examples of normalized SAXS XRD measurement data from the inoculated groups compared to the control group after 2 days, 4 days, and 16 days, respectively, with a sample to detector distance (S2d) of 160 mm. The SAXS XRD measurements from the control group all show a pronounced peak at a q of about 1.55 nm$^{-1}$.

Figure 9D:
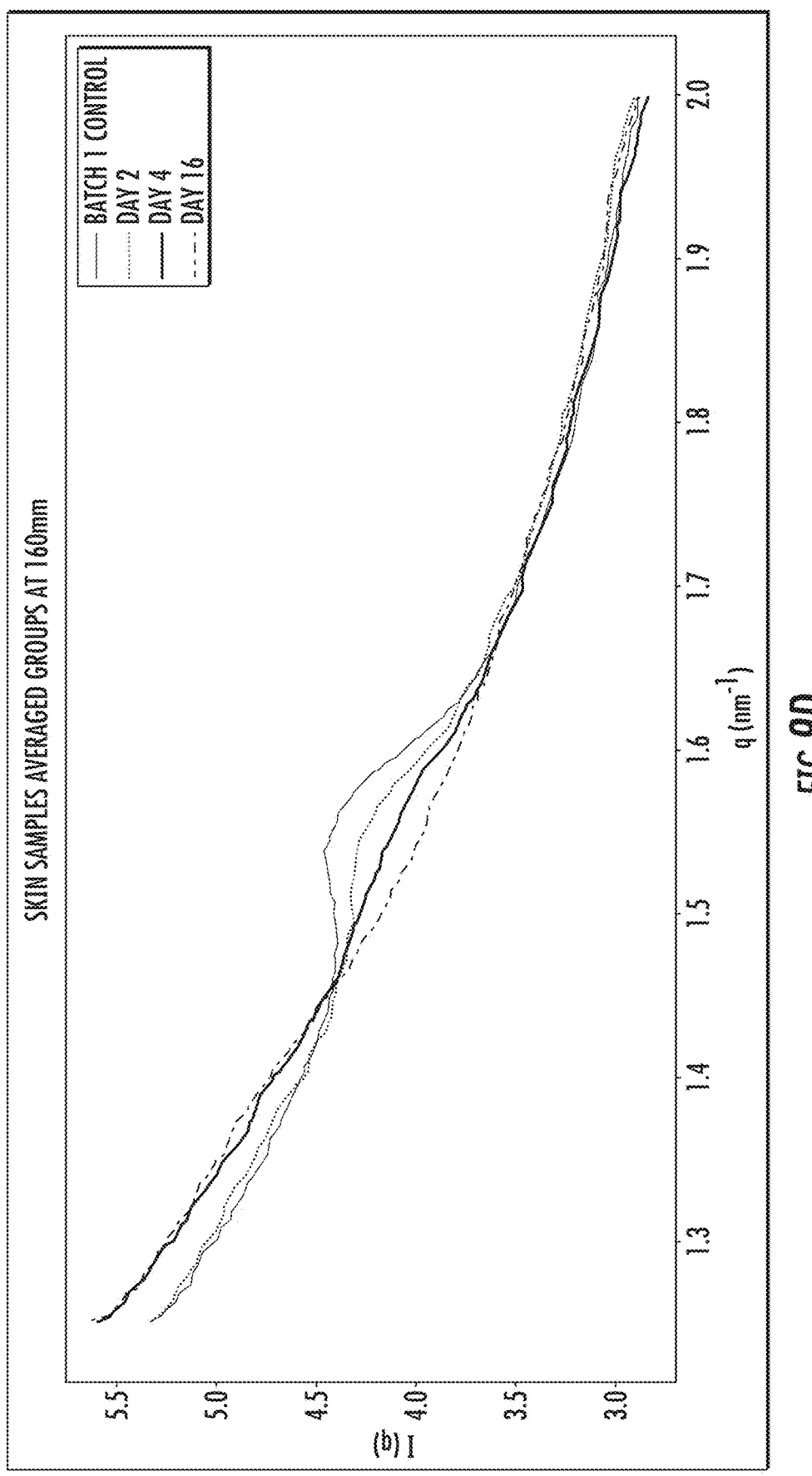
FIG. 9D shows the XRD measurement data from FIGS. 9A-9C, where the multiple XRD measurements shown in each of FIGS. 9A-9C were averaged for the control group and the inoculated groups after 2 days, 4 days, and 16 days.

FIG. 9D shows the XRD measurement data from FIGS. 9A-9C, where the multiple XRD measurements shown in each of FIGS. 9A-9C were averaged for the control group and the inoculated groups after 2 days, 4 days, and 16 days. The XRD measurement data from the inoculated groups shows a decrease in the 1.55 nm$^{-1}$ peak over time.

Figure 10A:
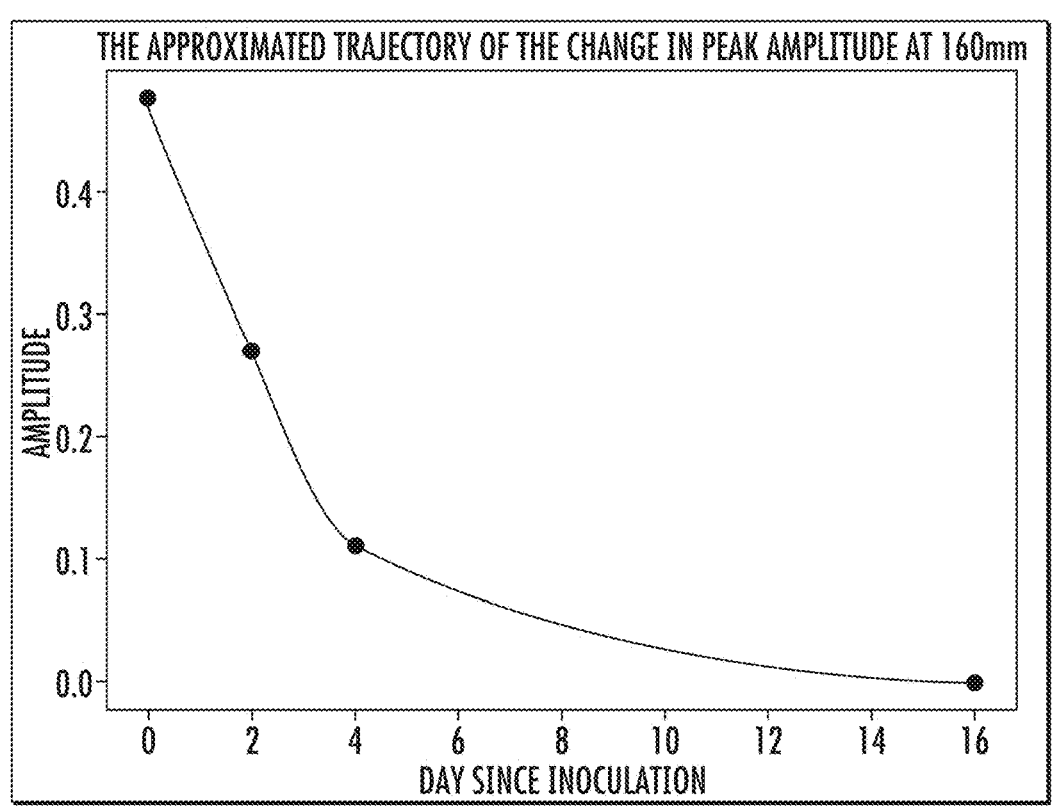
FIGS. 10A-10B show further analyses of the averaged XRD measurement data of FIG. 9D.
Figure 10B:
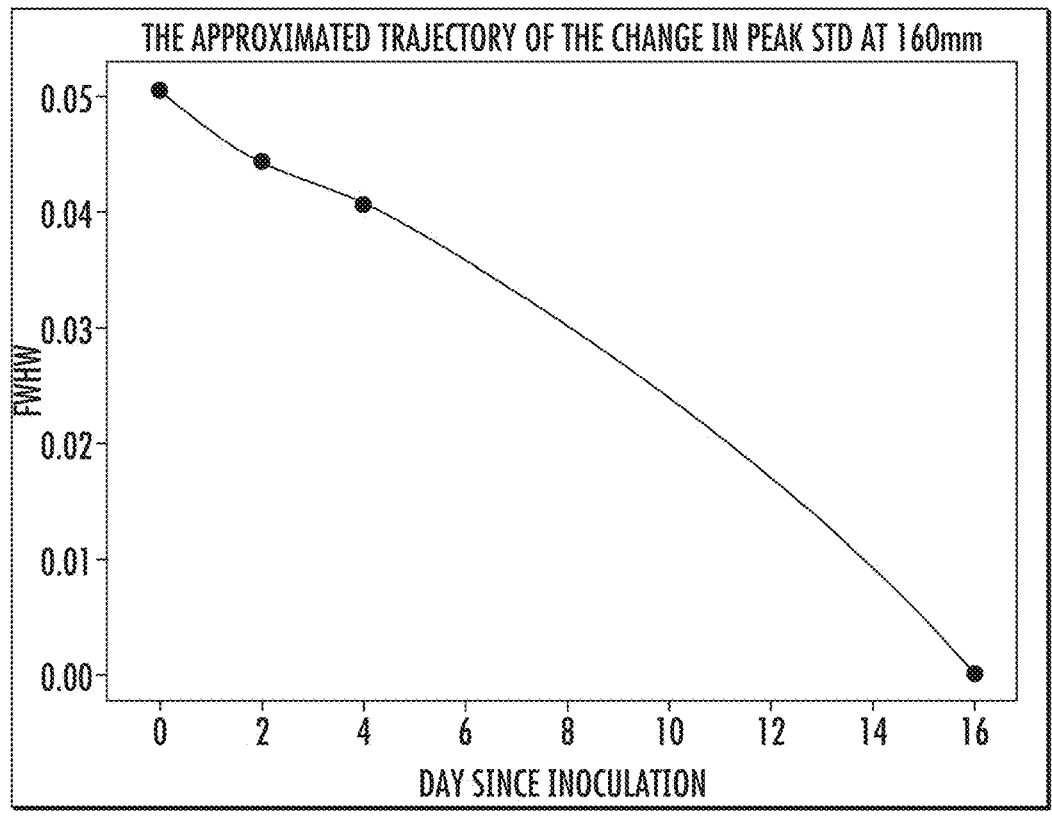

FIGS. 10A-10B show further analyses of the averaged XRD measurement data of FIG. 9D. The curves in FIG. 9D were fit using Gaussian peaks, and an amplitude and FWHM for each Gaussian was determined. FIGS. 10A-10B plot the amplitude and the standard deviation of the data in FIG. 9D at 1.55 nm$^{-1}$ for the control group (Day 0) and for the inoculated groups over time (Days 2, 4, and 16). The time-series trajectory data in each plot was then fit using a PCHIP. Therefore, FIGS. 10A-10B show an example where the normalized XRD measurement data was averaged, fit with Gaussian peaks, parameters of the Gaussian peaks were plotted, and the plotted parameters were fit with a function.

FIG. 10A shows the amplitude of the Gaussian peaks centered at about 1.55 nm$^{-1}$ over time for the control group (Day 0) and the inoculated groups (Day 2, 4, and 16). This analyzed XRD data shows that the amplitude of the Gaussian peaks centered at about 1.55 nm$^{-1}$ decreased over time for the inoculated groups.

FIG. 10B shows the FWHM of the Gaussian peaks centered at about 1.55 nm$^{-1}$ over time for the control group (Day 0) and the inoculated groups (Day 2, 4, and 16). This analyzed XRD data shows that the FWHM of the Gaussian peaks centered at about 1.55 nm$^{-1}$ decreased over time for the inoculated groups.

Figure 11:
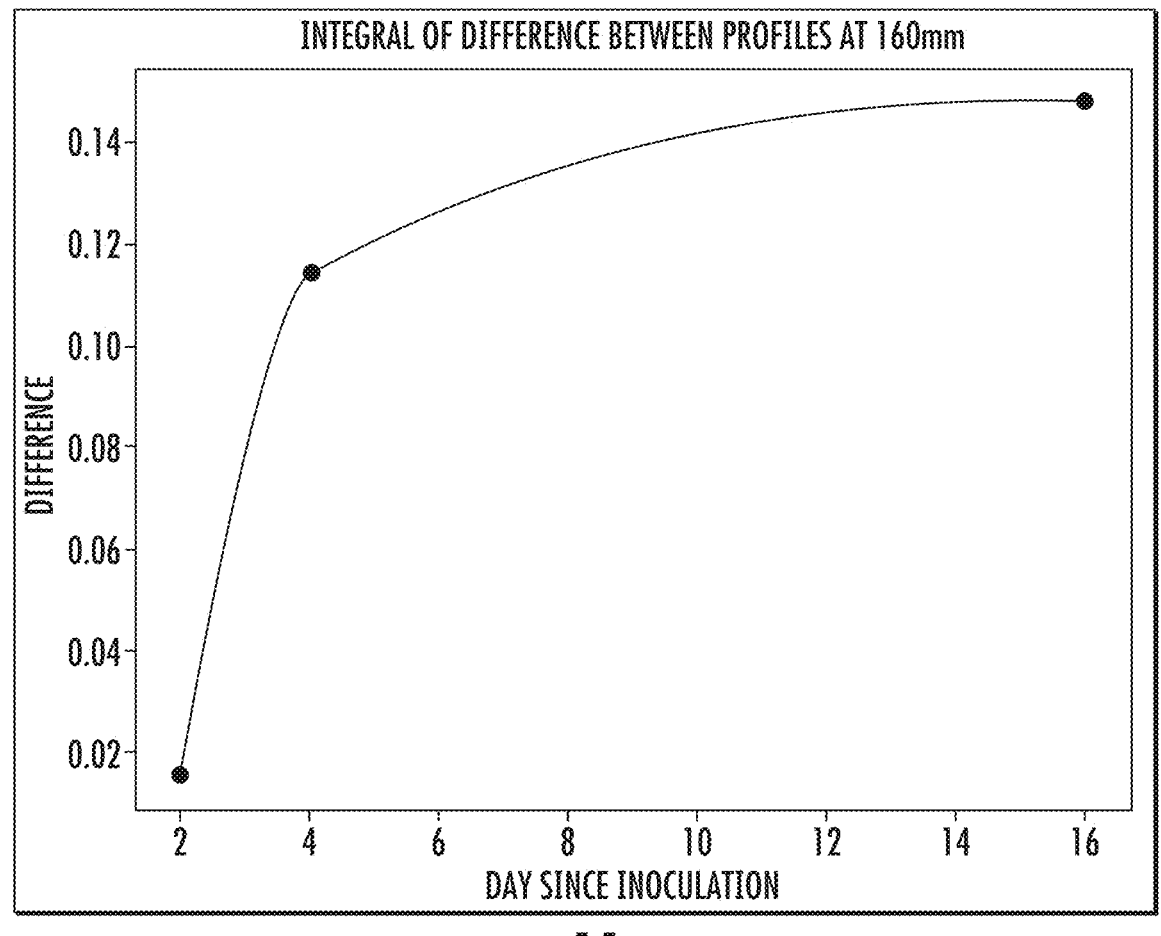
FIG. 11 shows another type of analysis of the averaged XRD measurement data of FIG. 9D.

FIG. 11 shows another type of analysis of the averaged XRD measurement data of FIG. 9D. The curves from the control group were subtracted from each of the curves of the inoculated groups, and then an integral of the difference between the XRD data curves was taken over the q range of 1.25 nm$^{-1}$ to 2 nm$^{-1}$. This procedure was done for the data after 2 days, 4 days, and 16 days to determine the difference in total normalized intensity between the XRD measurements of the control group and the inoculated groups over time. The analyzed data in FIG. 11 shows that the difference in XRD measurement data intensity between the inoculated groups and the control group increased over time (in a q range from 1.25 nm$^{-1}$ to 2 nm$^{-1}$).

The analyzed XRD measurement data in this Example, shown in FIGS. 7D, 8A-8E, 9D, 10A-10B, and 11 show that XRD measurements can be taken from tissue samples containing skin of the abdomen of mice who have been inoculated with prostate cancer, and that the XRD measurement data show an observable change. This observable change can be used to produce a quantitative diagnostic indicator that the mouse has cancer. Additionally, this Example shows that an observable change occurred within days of the mice being inoculated.

The XRD measurement data in this Example show that an XRD peak amplitude was reduced over time, as shown in FIGS. 8A and 10A. XRD peaks are caused by repeating regular crystalline structures with a particular d-spacing between diffraction planes determining the diffracted angle of the peak. Not to be limited by theory, a narrower FWHM of a peak can indicate a more ordered or more crystalline sample, and a broader FWHM can indicate a less ordered or more amorphous sample. The data in this Example (e.g., in FIGS. 8A-8B and 10A-10B) shows that the tissue of the skin of the abdomen of the inoculated mice became less crystalline and more amorphous than the tissue from the skin of the abdomen of the control mice over time, and that the amount of disorder increased over time in the inoculated mice. These results are surprising, since the XRD measurements were taken from tissue of the skin of the abdomen of the mice, while the mice were inoculated with cancer of a different organ (in this case prostate cancer).

The XRD measurements in this Example indicate that a quantitative diagnostic indicator could be determined based on an XRD peak amplitude being reduced and/or other XRD characteristics changing over time after inoculation.

The XRD measurements in this Example showed peaks at q of about 1.55 nm$^{-1}$, 13.5 nm$^{-1}$, and 19 nm$^{-1}$, which indicates that the XRD peaks may be attributable to adipose tissue containing lipids.

Example 2

Synchrotron X-ray diffraction studies of biological tissue samples of mice were performed at the Diamond Light Source (Oxford, UK).

The biological tissue samples studied included prostate tissue and skin from the abdomen of mice that were inoculated with prostate cancer and for a control group. SAXS studies were performed with a sample to detector distance of 160 mm and a q range from about 0 nm$^{-1}$ to 1.84 nm$^{-1}$, and WAXS studies were performed with a sample to detector distance of 20 mm and with a q range from 2 nm$^{-1}$ to 55.36 nm$^{-1}$ using the synchrotron radiation from the ALS at LBNL.

Figure 12A:
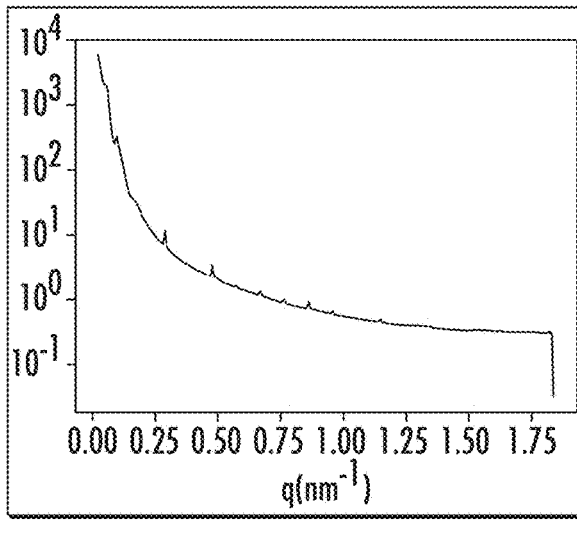
FIGS. 12A-12D show examples of experimental synchrotron SAXS results from skin samples of mice that were analyzed using different data processing methods.
Figure 12B:
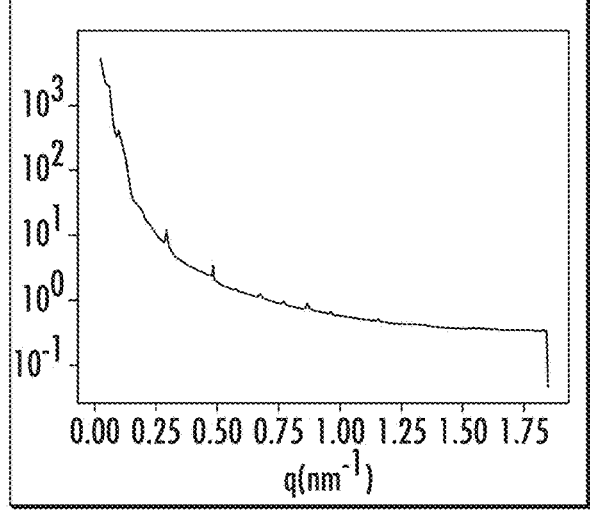
Figure 12C:
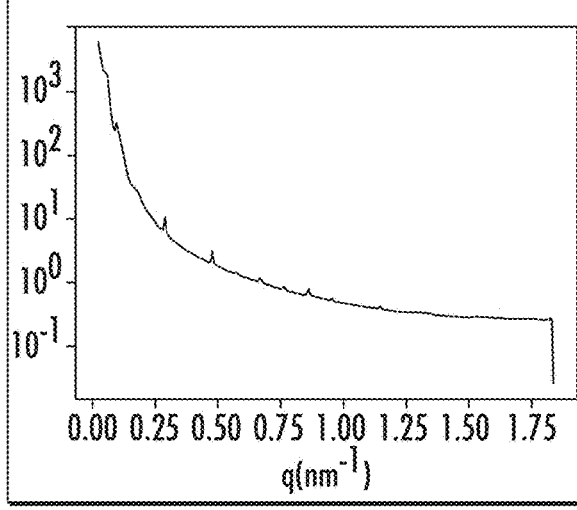
Figure 12D:
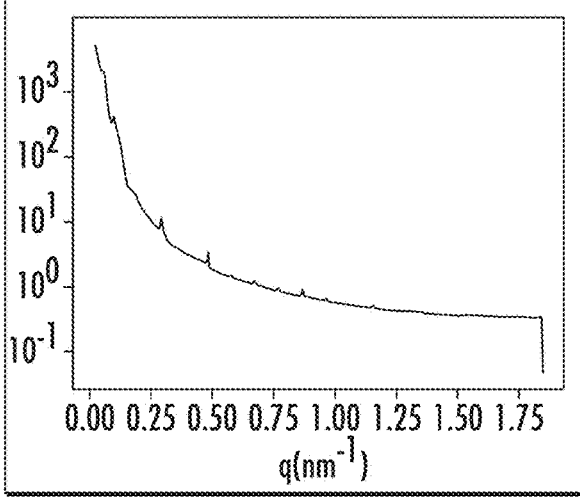

FIGS. 12A-12D show examples of experimental synchrotron SAXS results from skin samples of mice that were analyzed using different data processing methods. The y-axis is X-ray intensity in arbitrary units, and the x-axis is q in units of nm$^{-1}$. FIG. 12A includes an example of data from a single SAXS measurement with minimal processing. FIG. 12B includes an example of averaged data, where a plurality of measurements (like that shown in FIG. 12A) were averaged to produce the averaged data of FIG. 12B. FIG. 12C includes an example of subtracted data, where some sources of noise have been subtracted from a single measurement. FIG. 12D includes an example of averaged and subtracted data, where the averaging process used to generate the averaged data in FIG. 12B and the noise subtraction process used to generate the subtracted data of FIG. 12C have both been used to generate the averaged subtracted data of FIG. 12D.

Figure 13A:
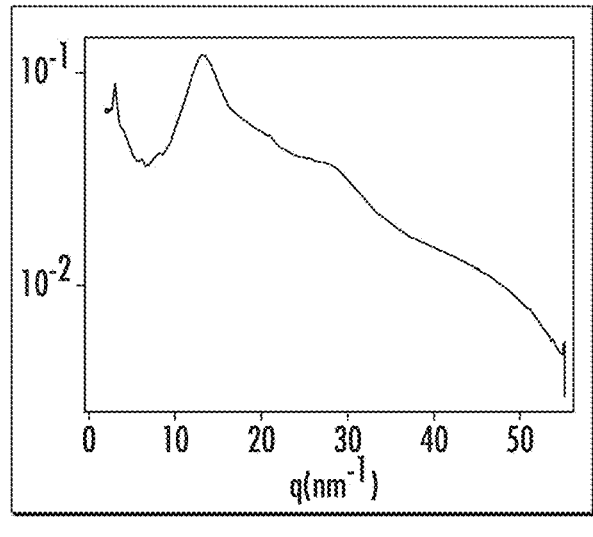
FIGS. 13A-13D show experimental synchrotron WAXS results from skin samples of mice with different data processing.
Figure 13B:
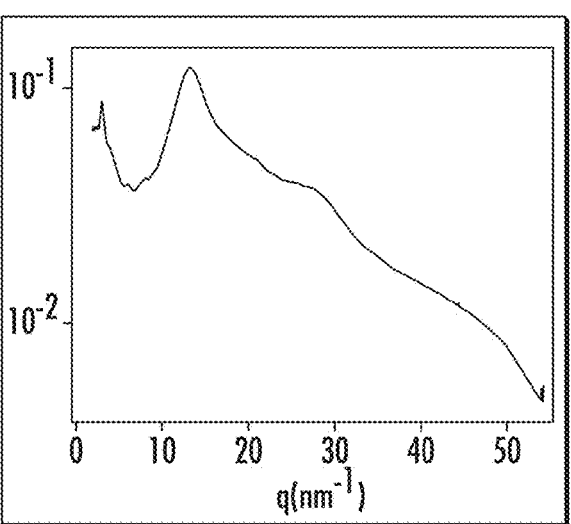
Figure 13C:
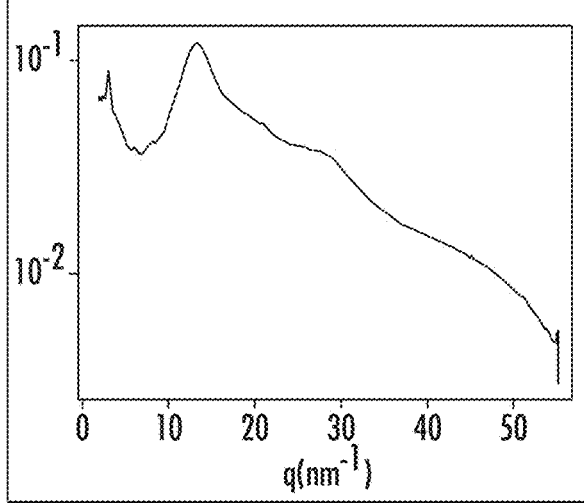
Figure 13D:
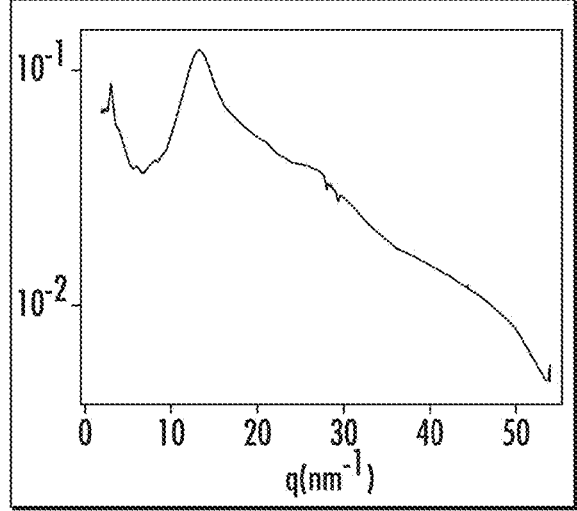

FIGS. 13A-13D show experimental synchrotron WAXS results from skin samples of mice with different data processing. The y-axis is X-ray intensity in arbitrary units, and the x-axis is q in units of nm$^{-1}$. FIG. 13A includes an example of data from a single WAXS measurement with minimal processing. FIG. 13B includes an example of averaged data, where a plurality of measurements (like that shown in FIG. 13A) were averaged to produce the averaged data of FIG. 13B. FIG. 13C includes an example of subtracted data, where some sources of noise have been subtracted from a single measurement. FIG. 13D includes an example of averaged and subtracted data where the averaging process used to generate the averaged data in FIG. 13B and the noise subtraction process used to generate the subtracted data of FIG. 13C have both been used to generate the averaged subtracted data of FIG. 13D.

FIGS. 14A-14K compare the synchrotron data of this Example with XRD data obtained using an X-ray diffractometer like that of FIG. 4 described in Example 1. The y-axis is X-ray intensity in arbitrary units and the x-axis is q in units of $nm^{-1}$ for these figures. In general, due to the high intensities of synchrotron radiation, the sensitivity and the spectral resolution are better than those of XRD data obtained using an X-ray diffractometer like that of FIG. 4.

Figure 14A:
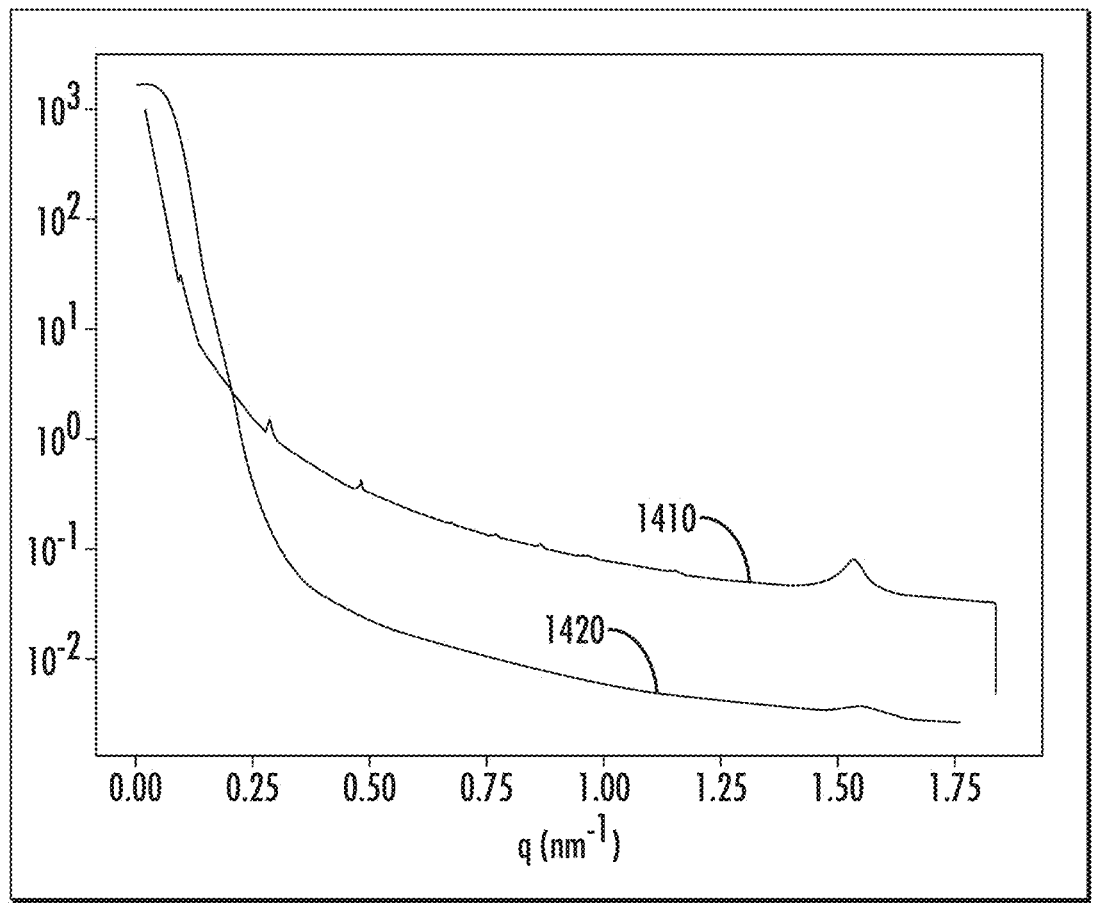

FIG. 14A shows example synchrotron SAXS data 1410 overlayed with example X-ray diffractometer SAXS data 1420, where both data curves represent measured skin samples of mice. Both curves show a peak at round 1.55 $nm^{-1}$. Due to the higher sensitivity, the synchrotron SAXS data 1410 showed additional small features (e.g., around 0.25 $nm^{-1}$ and 0.5 $nm^{-1}$) that were not observed in the X-ray diffractometer SAXS data 1420.

Figure 14B:
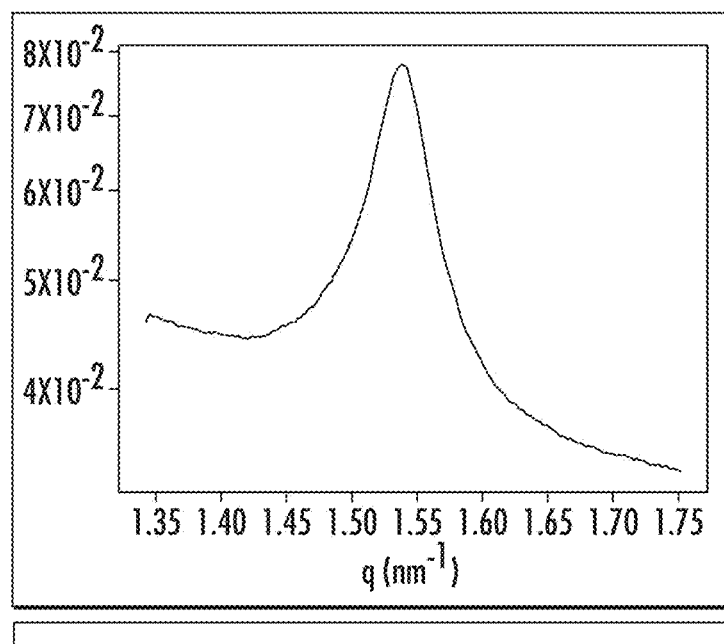
Figure 14C:
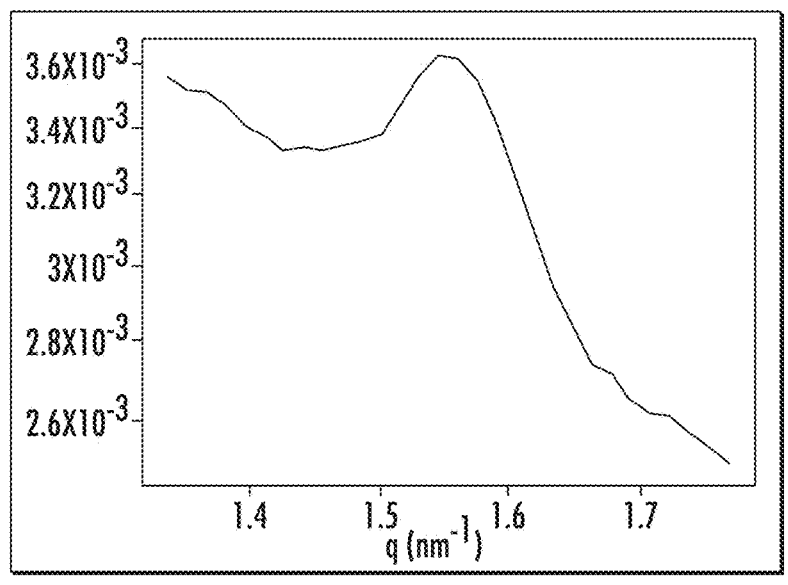
Figure 14D:
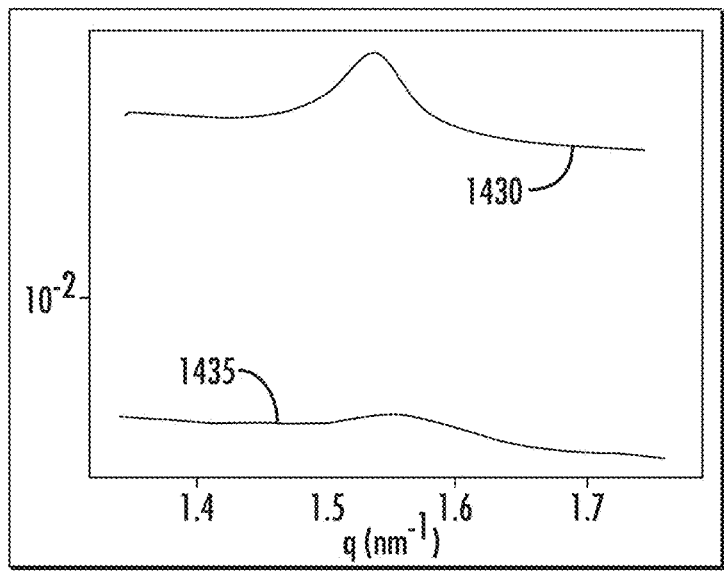

FIGS. 14B-14D show SAXS data of skin samples of mice with zoomed in q regions from 1.35 $nm^{-1}$ to 1.75 $nm^{-1}$. FIG. 14B shows an example of synchrotron SAXS data, FIG. 14C shows an example of X-ray diffractometer SAXS data, and FIG. 14D shows an example of synchrotron SAXS data 1430 and X-ray diffractometer SAXS data 1435 overlayed. The prominent peak at q of about 1.55 $nm^{-1}$ was observed using both SAXS techniques for these samples.

FIGS. 14E-14G show WAXS data of skin samples of mice over a q range from about 2.5 $nm^{-1}$ to about 21 $nm^{-1}$. FIG. 14E shows an example of synchrotron WAXS data, FIG. 14F shows an example of X-ray diffractometer WAXS data, and FIG. 14G shows an example of synchrotron WAXS data 1440 and X-ray diffractometer WAXS data 1445 overlayed. A peak at q of about 13.5 $nm^{-1}$ and a peak at a q of about 19 $nm^{-1}$ were observed using both WAXS techniques.

Figure 14H:
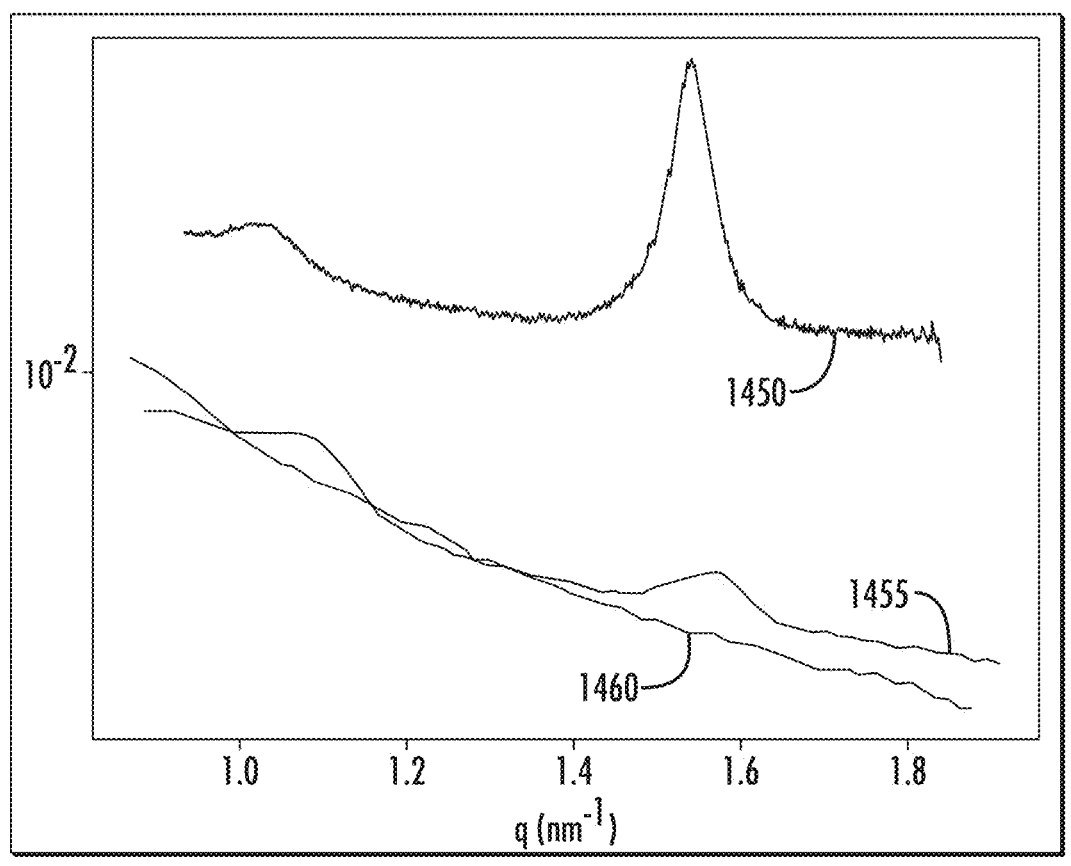

FIG. 14H shows example synchrotron SAXS data 1450 overlayed with example X-ray diffractometer SAXS data 1455 and 1460 taken from the prostate samples of mice. The synchrotron SAXS data 1450 and the X-ray diffractometer SAXS data 1455 showed peaks at q of around 1.1 $nm^{-1}$ and 1.55 $nm^{-1}$. However, these peaks were not observed in the X-ray diffractometer SAXS data 1460.

Figure 14I:
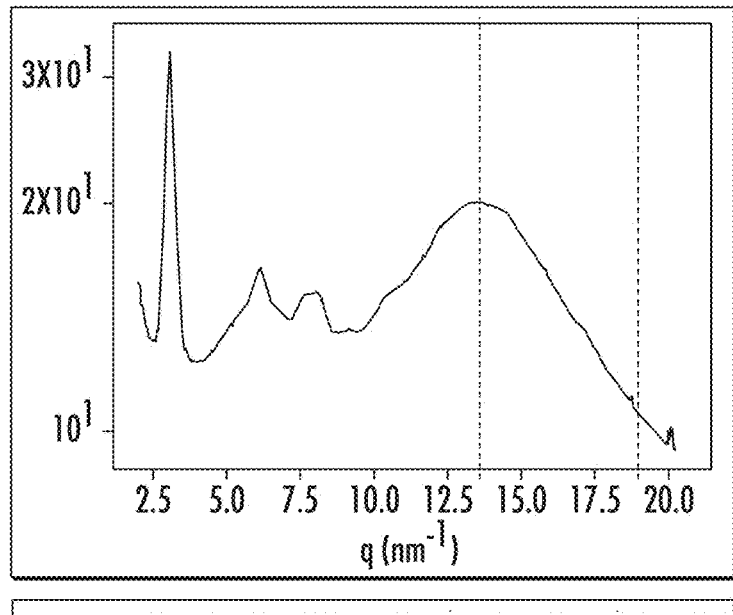
Figure 14J:
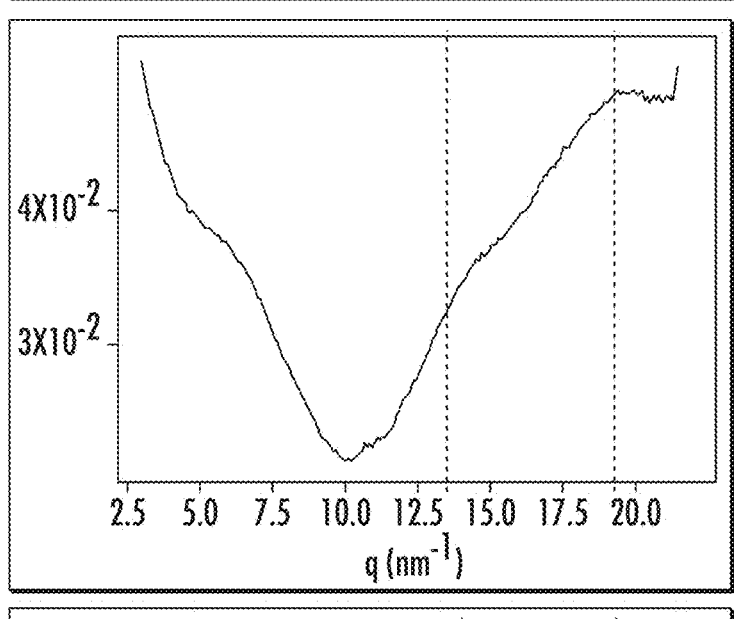
Figure 14K:
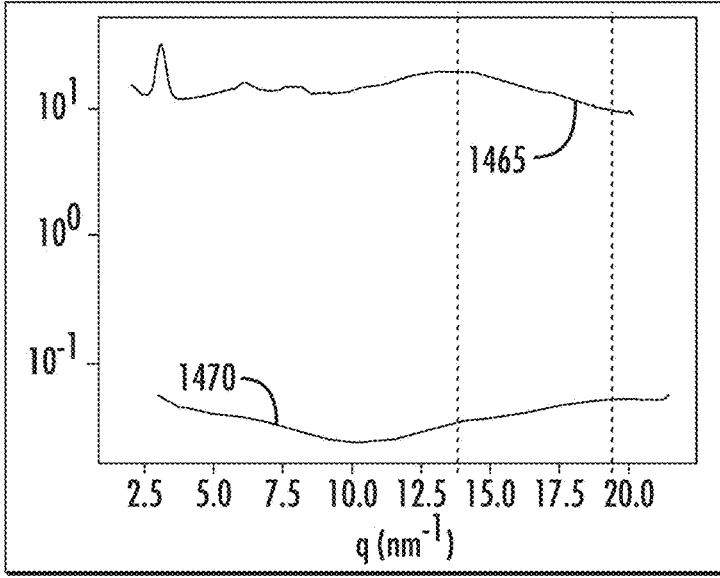
Figure 15A:
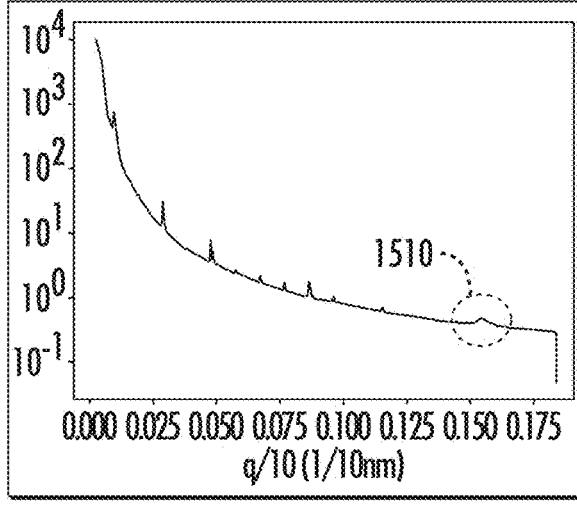
FIGS. 15A-15D show examples of synchrotron SAXS results from skin samples of mice over time.
Figure 15B:
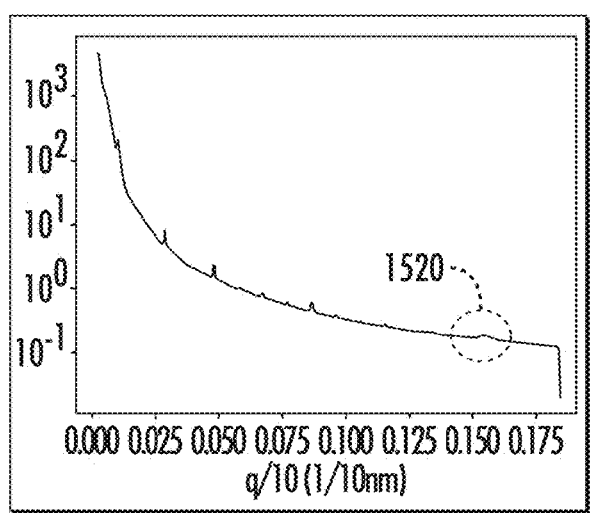
Figure 15C:
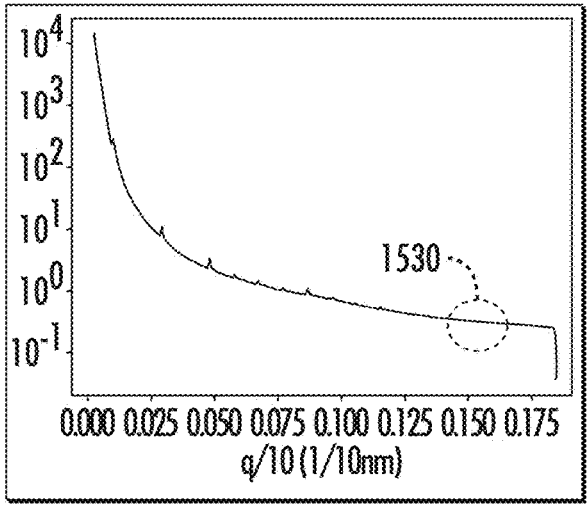
Figure 15D:
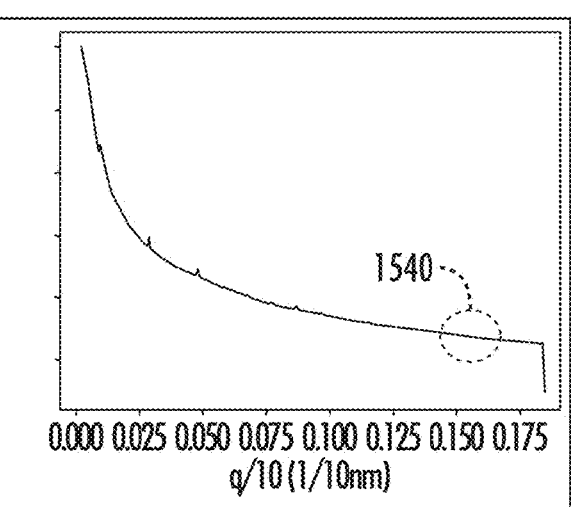

FIGS. 14I-14K show WAXS data of prostate samples of mice with q ranges from about 2.5 $nm^{-1}$ to about 21 $nm^{-1}$. FIG. 14I shows an example of synchrotron WAXS data, FIG. 14J shows an example of X-ray diffractometer WAXS data, and FIG. 14K shows an example of synchrotron WAXS data 1465 and X-ray diffractometer WAXS data 1470 overlayed. A peak at q of about 13.5 $nm^{-1}$ was observed using both WAXS techniques for these samples.

FIGS. 15A-15D show examples of synchrotron SAXS results from skin samples of mice over time. The y-axis is X-ray intensity in arbitrary units and the x-axis is q/10 in units of $\frac{1}{10}$ nm. The synchrotron SAXS data in these figures has been averaged and subtracted, as described with respect to FIG. 12D. The data in FIG. 15A was taken from the control group, the data in FIG. 15B was taken 2 days after inoculation with prostate cancer, the data in FIG. 15C was taken 4 days after inoculation with prostate cancer, and the data in FIG. 15D was taken 16 days after inoculation with prostate cancer. The data in FIGS. 15A-15D each show a peak at a q of about 1.55 $nm^{-1}$, and the intensity of the peak was observed to generally decrease over time. In other words, the intensity of peak 1510 was larger than the intensity of peak 1520, which was larger than the intensity of peak 1530, and at 16 days there is almost no peak in region 1540.

Figure 16A:
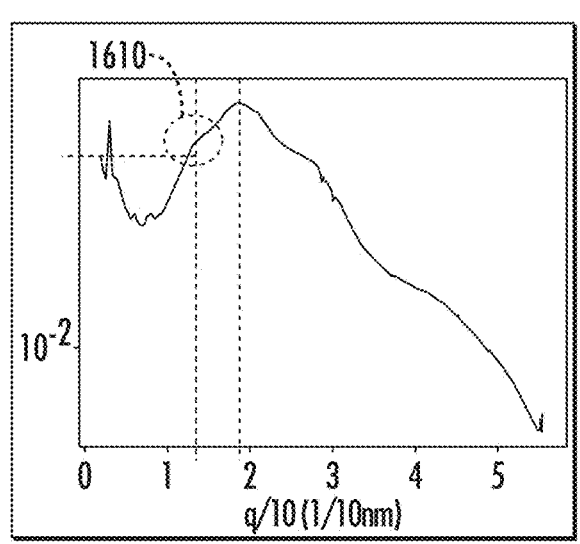
FIGS. 16A-16D show examples of synchrotron WAXS results from skin samples of mice over time.
Figure 16B:
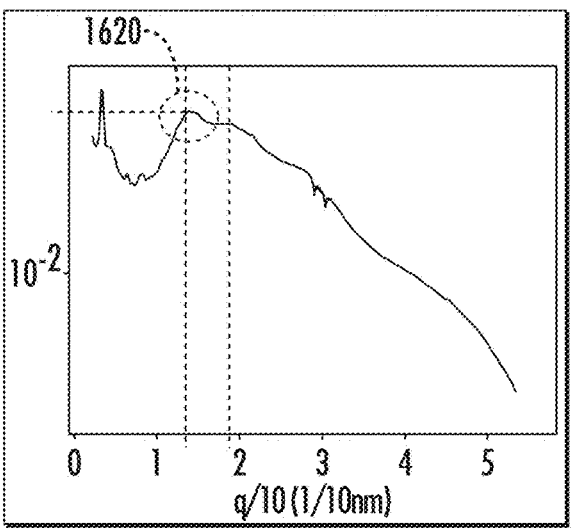
Figure 16C:
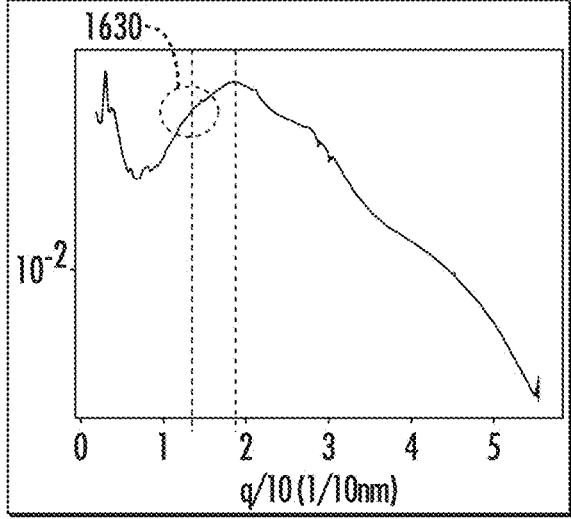
Figure 16D:
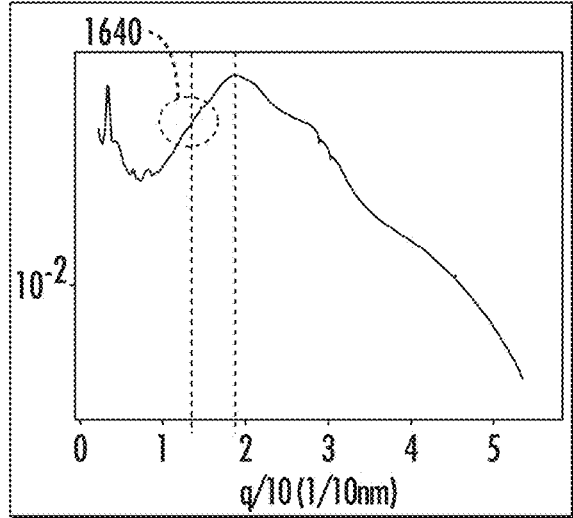

FIGS. 16A-16D show examples of synchrotron WAXS results from skin samples of mice over time. The y-axis is X-ray intensity in arbitrary units, and the x-axis is q/10 in units of $\frac{1}{10}$ nm. The synchrotron WAXS data in these figures has been averaged and subtracted, as described with respect to FIG. 13D. The data in FIG. 16A was taken from the control group, the data in FIG. 16B was taken 2 days after inoculation with prostate cancer, the data in FIG. 16C was taken 4 days after inoculation with prostate cancer, and the data in FIG. 16D was taken 16 days after inoculation with prostate cancer. The data in FIGS. 16A-16D each show a peak at a q of about 13.5 $nm^{-1}$ and a peak at a q of about 19 $nm^{-1}$. The intensity of the peak at a q of about 13.5 $nm^{-1}$ was observed to generally decrease over time in this Example. For example, the peak 1610 (which appears as a prominent shoulder since it is close to larger peak at about 19 $nm^{-1}$) appears to be larger than the peak 1630 (which appears as less of a shoulder). Peak 1630 also appears to be larger than the peak 1640 (which barely appears as a shoulder at all). The synchrotron WAXS data after 2 days in FIG. 16B is somewhat different than the data in FIGS. 16A, 16C, and 16D in that the intensity of the peak 1620 at a q of about 13.5 $nm^{-1}$ is larger than the intensity of the peak at a q of about 19 $nm^{-1}$. This peak ratio difference in the data in FIG. 16B makes the peak at 13 $nm^{-1}$ more difficult to compare with the data in FIGS. 16A, 16C and 16D.

The synchrotron SAXS and WAXS measurement data in this Example, shown in FIGS. 12A-16D, show that synchrotron XRD measurements can be taken from tissue samples containing skin of the abdomen of mice who have been inoculated with prostate cancer, and that the synchrotron XRD measurement data show an observable change. This observable change can be used to produce a quantitative diagnostic indicator that the mouse has cancer. Additionally, an observable change occurred within days of the mice being inoculated.

The synchrotron SAXS and WAXS measurement data in this Example also showed many of the same trends as the XRD data described in Example 1 that was obtained using a tissue diffractometer (e.g., as shown in FIG. 4), and indicate that a quantitative diagnostic indicator could be determined based on an XRD peak amplitude being reduced over time after inoculation.

Similar to the data in Example 1, the synchrotron SAXS and WAXS measurement data in this Example showed peaks at q of about 1.55 $nm^{-1}$, 13.5 $nm^{-1}$, and 19 $nm^{-1}$ which indicates that the XRD peaks may be attributable to adipose tissue containing lipids.

Embodiments

Clause 1. A system comprising: a fixture configured to position a region of skin of a patient within a measurement region; an X-ray source coupled to the fixture and configured to emit an X-ray beam that overlaps with the measurement region; an X-ray receiver coupled to the fixture, the X-ray receiver comprising a coordinate-sensitive digital detector of X-rays; and one or more processors coupled to the X-ray receiver; wherein the one or more processors are configured to control the X-ray source and the X-ray receiver, to collect X-ray diffraction data from the X-ray receiver, to process the X-ray diffraction data, and to determine a diagnostic indicator for assessment of a physiological or pathological condition based on the processed X-ray diffraction data.

Clause 2. The system of clause 1, wherein the diagnostic indicator comprises a probability score for a likelihood of one or more physiological or pathological conditions.

Clause 3. The system of any of clauses 1-2, wherein the fixture is configured to position skin between fingers of a patient or a thenar web space of a patient within a measurement region.

Clause 4. The system of any of clauses 1-2, wherein the X-ray source emits incident X-rays that interact with the region of skin in the measurement region, and wherein the fixture is configured to position a surface of the region of skin such that a relative position and orientation between the incident X-rays and a surface of the region of skin is configured for grazing incidence X-ray diffraction.

Clause 5. The system of clause 4, wherein the fixture further comprises a block stop with a flat surface approximately parallel with the incident X-rays, that is located adjacent to the measurement region.

Clause 6. The system of any of clauses 1-5, wherein the X-ray receiver is configured to detect the X-rays in a q range less than about 2 $nm^{-1}$, or from about 1 $nm^{-1}$ to about 2 $nm^{-1}$.

Clause 7. The system of any of clauses 1-5, wherein the X-ray receiver is configured to detect the X-rays in a q range from about 2 $nm^{-1}$ to about 50 $nm^{-1}$, or from about 10 $nm^{-1}$ to about 20 $nm^{-1}$.

Clause 8. The system of any of clauses 1-7, wherein the X-ray source further comprises: an X-ray radiation source that forms a mono-energetic radiation spectrum; a collimating aperture; and a first monochromator; wherein the X-ray source is configured to emit a collimated X-ray beam with an approximately rectangular or circular cross-section.

Clause 9. The system of clause 8, wherein the first monochromator is a highly ordered pyrolytic graphite (HOPG) monochromator or a multilayer monochromator.

Clause 10. The system of any of clauses 1-9, wherein the X-ray source further comprises a parabolic shaped multilayer mirror that converts divergent X-rays into collimated parallel X-rays.

Clause 11. The system of any of clauses 1-10, wherein the X-ray source further comprises an adjustable diaphragm that allows the X-ray source to be a small-angle X-ray source.

Clause 12. The system of any of clauses 1-11, wherein a distance between the measurement region and the X-ray receiver is adjustable.

Clause 13. The system of any of clauses 1-12, wherein the X-ray source further comprises a beam forming apparatus comprising a Kratki or Montel mirror collimator.

Clause 14. The system of any of clauses 1-13, wherein the fixture further comprises a clamping mechanism comprising an incident-side part and an exit-side part coupled to a pivot mechanism, wherein the incident-side part and the exit-side part each comprise a stop which are configured to contact one another and form a consistent spacing between the incident-side part and the exit-side part when closed, and wherein the incident-side part and the exit-side part each comprise a window that is substantially transparent to X-rays.

Clause 15. The system of any of clauses 1-13, wherein the fixture further comprises an incident-side part and an exit-side part rigidly coupled to a block forming a consistent spacing between the incident-side part and the exit-side part, wherein the incident-side part and the exit-side part each comprise a window that is substantially transparent to X-rays.

Clause 16. A method for processing X-ray diffraction data comprising: emitting X-rays from an X-ray source; diffracting the X-rays from of a region of skin of a patient using a system comprising a fixture configured to position the region of skin of the patient within a measurement region; detecting diffracted X-rays using an X-ray receiver coupled to the fixture, the X-ray receiver comprising a coordinate-sensitive digital detector of X-rays; and processing X-ray diffraction data from the coordinate-sensitive digital detector of X-rays using one or more processors coupled to the X-ray receiver to determine a diagnostic indicator for assessment of one or more physiological or pathological conditions.

Clause 17. The method of clause 16, wherein the processing the X-ray diffraction data from the coordinate-sensitive digital detector of X-rays comprises analyzing an X-ray diffraction intensity of an X-ray diffraction pattern to determine a molecular structure of the skin.

Clause 18. The method of clause 16, wherein the X-ray receiver detects the X-rays in a q range less than about 2 $nm^{-1}$, or from about 1 $nm^{-1}$ to about 2 $nm^{-1}$.

Clause 19. The method of clause 16, wherein the X-ray receiver detects the X-rays in a q range from about 2 $nm^{-1}$ to about 50 $nm^{-1}$, or from about 10 $nm^{-1}$ to about 20 $nm^{-1}$.

Clause 20. A method for processing X-ray diffraction data comprising: measuring a first molecular structure of a region of skin of a patient at a first time and measuring a second molecular structure of the region of skin of the patient at a second time using a tissue diffractometer comprising a fixture configured to position the region of skin within a measurement region; observing a change between the first molecular structure and the second molecular structure; and determining the diagnostic indicator for assessment of one or more physiological or pathological conditions based on the observed change between the first molecular structure and the second molecular structure.

Clause 21. The method of clause 20, wherein the observing a change between the first molecular structure and the second molecular structure comprises analyzing X-ray diffraction intensities of X-ray diffraction patterns taken at the first time and the second time.

Clause 22. The method of clause 20, wherein the tissue diffractometer further comprises an X-ray receiver that detects the X-rays in a q range less than about 2 $nm^{-1}$, or from about 1 $nm^{-1}$ to about 2 $nm^{-1}$.

Clause 23. The method of clause 20, wherein the tissue diffractometer further comprises an X-ray receiver that detects the X-rays in a q range from about 2 $nm^{-1}$ to about 50 $nm^{-1}$, or from about 10 $nm^{-1}$ to about 20 $nm^{-1}$.

Clause 24. A method for processing X-ray diffraction data comprising: controlling a tissue diffractometer using a processor to perform an X-ray diffraction (XRD) measurement to measure a molecular structure of a biological tissue sample including skin, wherein the tissue diffractometer comprises a fixture configured to position the sample within a measurement region; processing XRD data of the sample using the processor, or using a second processor; determining a change of the molecular structure of the sample based on the processed XRD data using the processor or the second processor; determining diagnostic indicator for assessment of one or more physiological or pathological conditions, based on the change of the molecular structure of the sample using the processor or the second processor.

Clause 25. The method of clause 24, wherein the processing the XRD data comprises analyzing an X-ray diffraction intensity of an X-ray diffraction pattern to determine the molecular structure of the sample.

Clause 26. The method of clause 24, wherein the XRD data comprises data in a q range less than about 2 $nm^{-1}$, or from about 1 $nm^{-1}$ to about 2 $nm^{-1}$.

Clause 27. The method of clause 24, wherein the XRD data comprises data in a q range from about 2 nm$^{-1}$ to about 50 nm$^{-1}$, or from about 10 nm$^{-1}$ to about 20 nm$^{-1}$.

Clause 28. A non-transitory machine-readable medium storing instructions which when executed cause one or more processors to perform operations comprising: controlling a tissue diffractometer to perform an X-ray diffraction (XRD) measurement to measure a molecular structure of a biological tissue sample including skin, wherein the tissue diffractometer comprises a fixture configured to position the sample within a measurement region; processing XRD data of the sample; determining a change of the molecular structure of the sample based on the processed XRD data; determining diagnostic indicator for assessment of one or more physiological or pathological conditions, based on the change of the molecular structure of the sample.

Clause 29. The non-transitory machine-readable medium of clause 28, wherein the processing the XRD data comprises analyzing an X-ray diffraction intensity of an X-ray diffraction pattern to determine the molecular structure of the sample.

Clause 30. The non-transitory machine-readable medium of clause 28, wherein the XRD data comprises data in a q range less than about 2 nm$^{-1}$, or from about 1 nm$^{-1}$ to about 2 nm$^{-1}$.

Clause 31. The non-transitory machine-readable medium of clause 28, wherein the XRD data comprises data in a q range from about 2 nm$^{-1}$ to about 50 nm$^{-1}$, or from about 10 nm$^{-1}$ to about 20 nm$^{-1}$.

Clause 32. A system comprising: a fixture configured to position a region of skin of a patient within a measurement region; an X-ray source coupled to the fixture and configured to emit an X-ray beam that overlaps with the measurement region, wherein the X-ray source is configured to emit a collimated X-ray beam with an approximately rectangular or circular cross-section, and wherein the X-ray source comprises: an X-ray radiation source that forms a mono-energetic radiation spectrum; a collimating aperture; and a first monochromator; an X-ray receiver coupled to the fixture, the X-ray receiver comprising a coordinate-sensitive digital detector of X-rays; and one or more processors coupled to the X-ray receiver, wherein the one or more processors are configured to control the X-ray source and the X-ray receiver, to collect X-ray diffraction data from the X-ray receiver, to process the X-ray diffraction data, and to determine a diagnostic indicator comprising a probability score for a likelihood of one or more physiological or pathological conditions, based on the processed X-ray diffraction data.

Reference has been made to embodiments of the disclosed invention. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A system comprising:
a fixture configured to position a region of skin of a patient within a measurement region;
an X-ray source coupled to the fixture and configured to emit an X-ray beam that overlaps with the measurement region;
an X-ray receiver coupled to the fixture, the X-ray receiver comprising a coordinate-sensitive digital detector of X-rays; and
one or more processors coupled to the X-ray receiver;
wherein the one or more processors are configured to control the X-ray source and the X-ray receiver, to collect X-ray diffraction data from the X-ray receiver, to process the X-ray diffraction data, and to determine a diagnostic indicator for assessment of a physiological or pathological condition based on the processed X-ray diffraction data, and
wherein the X-ray source emits incident X-rays that interact with the region of skin in the measurement region, and wherein the fixture is configured to position a surface of the region of skin such that a relative position and orientation between the incident X-rays and a surface of the region of skin is configured for grazing incidence X-ray diffraction.

2. The system of claim 1, wherein the diagnostic indicator comprises a probability score for a likelihood of the physiological or pathological condition.

3. The system of claim 1, wherein the fixture further comprises a block stop with a flat surface approximately parallel with the incident X-rays, that is located adjacent to the measurement region.

4. The system of claim 1, wherein the X-ray receiver is configured to detect the X-rays in a q range less than about 2 nm$^{-1}$, or from about 1 nm$^{-1}$ to about 2 nm$^{-1.}$ 5. The system of claim 1, wherein the X-ray receiver is configured to detect the X-rays in a q range from about 2 nm$^{-1}$ to about 50 nm$^{-1}$, or from about 10 nm$^{-1}$ to about 20 nm$^{-1.}$ 6. The system of claim 1, wherein the X-ray source further comprises:
an X-ray radiation source that forms a mono-energetic radiation spectrum;
a collimating aperture; and
a first monochromator;
wherein the X-ray source is configured to emit a collimated X-ray beam with an approximately rectangular or circular cross-section.

7. The system of claim 6, wherein the first monochromator is a highly ordered pyrolytic graphite (HOPG) monochromator or a multilayer monochromator.

8. The system of claim 1, wherein the X-ray source further comprises a parabolic shaped multilayer mirror that converts divergent X-rays into collimated parallel X-rays.

9. The system of claim 1, wherein the X-ray source further comprises an adjustable diaphragm that allows the X-ray source to be a small-angle X-ray source.

10. The system of claim 1, wherein a distance between the measurement region and the X-ray receiver is adjustable.

11. The system of claim 1, wherein the X-ray source further comprises a beam forming apparatus comprising a Kratki or Montel mirror collimator.

12. A system comprising:

a fixture configured to position a region of skin of a patient within a measurement region;

an X-ray source coupled to the fixture and configured to emit an X-ray beam that overlaps with the measurement region, wherein the X-ray source is configured to emit a collimated X-ray beam with an approximately rectangular or circular cross-section, and wherein the X-ray source comprises:

an X-ray radiation source that forms a mono-energetic radiation spectrum;

a collimating aperture; and a first monochromator;

an X-ray receiver coupled to the fixture, the X-ray receiver comprising a coordinate-sensitive digital detector of X-rays; and one or more processors coupled to the X-ray receiver, wherein the one or more processors are configured to control the X-ray source and the X-ray receiver, to collect X-ray diffraction data from the X-ray receiver, to process the X-ray diffraction data, and to determine a diagnostic indicator comprising a probability score for a likelihood of one or more physiological or pathological conditions, based on the processed X-ray diffraction data, wherein the X-ray source emits incident X-rays that interact with the region of skin in the measurement region, and wherein the fixture is configured to position a surface of the region of skin such that a relative position and orientation between the incident X-rays and a surface of the region of skin is configured for grazing incidence X-ray diffraction.

13. The system of claim 12, wherein the fixture further comprises a block stop with a flat surface approximately parallel with the incident X-rays, that is located adjacent to the measurement region.

\* \* \* \* \*